United States Patent
Baker, Jr. et al.

(10) Patent No.: US 7,130,671 B2
(45) Date of Patent: Oct. 31, 2006

(54) PULSE OXIMETER SENSOR OFF DETECTOR

(75) Inventors: Clark R. Baker, Jr., Castro Valley, CA (US); Thomas J. Yorkey, San Ramon, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 284 days.

(21) Appl. No.: 10/775,497

(22) Filed: Feb. 9, 2004

(65) Prior Publication Data

US 2004/0158135 A1 Aug. 12, 2004

Related U.S. Application Data

(63) Continuation of application No. 09/876,004, filed on Jun. 6, 2001, now Pat. No. 6,721,584, which is a continuation of application No. 09/435,144, filed on Nov. 5, 1999, now abandoned, which is a continuation of application No. 09/137,479, filed on Aug. 20, 1998, now Pat. No. 6,083,172, which is a continuation of application No. 08/660,510, filed on Jun. 7, 1996, now Pat. No. 5,853,364.

(60) Provisional application No. 60/000,195, filed on Jun. 14, 1995.

(51) Int. Cl.
*A61B 5/00* (2006.01)
(52) U.S. Cl. ........................... 600/310; 600/323
(58) Field of Classification Search ............... 600/310, 600/322, 323, 330, 336
See application file for complete search history.

(56) References Cited

U.S. PATENT DOCUMENTS

| 3,647,299 A | 3/1972 | Lavallee |
| 3,704,706 A | 12/1972 | Herczfeld et al. |
| 4,063,551 A | 12/1977 | Sweeney |

(Continued)

FOREIGN PATENT DOCUMENTS

DE 33288862 A1 2/1985

(Continued)

OTHER PUBLICATIONS

Mook et al., "Wavelength dependency of the spectrophotometric determination of blood oxygen saturation," *Clinical Chemistry Acta*, 26:170-173 (1969).

(Continued)

*Primary Examiner*—Eric F. Winakur
(74) *Attorney, Agent, or Firm*—Fletcher Yoder P.C.

(57) ABSTRACT

In a system for measuring a physiological parameter using at least one wavelength of electromagnetic energy transmitted through living tissue, a method for determining an operational status of the system. The method includes receiving a data signal from at least one sensor, determining whether the received data signal is representative of the physiological parameter by sensing whether the at least one sensor is secured to the living tissue, and generating a status signal representative of the operational status of the system based on that determination. The determination includes measuring an output level corresponding to the at least one wavelength. The determination may also include analyzing a spectrum corresponding to the at least one wavelength to determine a percentage of energy contained in a subset of the spectrum, or monitoring an amplitude of the data signal for a given interval.

5 Claims, 12 Drawing Sheets

U.S. PATENT DOCUMENTS

| | | |
|---|---|---|
| 4,086,915 A | 5/1978 | Kofsky et al. |
| 4,095,117 A | 6/1978 | Nagy |
| 4,266,554 A | 5/1981 | Hamaguri |
| 4,407,290 A | 10/1983 | Wilber |
| 4,537,200 A | 8/1985 | Widrow |
| 4,549,551 A | 10/1985 | Dyck et al. |
| 4,603,700 A * | 8/1986 | Nichols et al. ............ 600/331 |
| 4,621,643 A | 11/1986 | New et al. |
| 4,649,505 A | 3/1987 | Zinser, Jr. et al. |
| 4,700,708 A | 10/1987 | New, Jr. et al. |
| 4,705,049 A | 11/1987 | John |
| 4,723,294 A | 2/1988 | Taguchi |
| 4,763,282 A | 8/1988 | Rosenberg |
| 4,770,179 A | 9/1988 | New, Jr. et al. |
| 4,773,422 A | 9/1988 | Isaacson et al. |
| 4,799,493 A | 1/1989 | DuFault |
| 4,800,495 A | 1/1989 | Smith |
| 4,802,486 A | 2/1989 | Goodman et al. |
| 4,817,013 A | 3/1989 | Corenman et al. |
| 4,819,752 A | 4/1989 | Zelin |
| 4,824,242 A | 4/1989 | Frick et al. |
| 4,848,901 A | 7/1989 | Hood, Jr. |
| 4,860,759 A | 8/1989 | Kahn et al. |
| 4,863,265 A | 9/1989 | Flower et al. |
| 4,867,571 A | 9/1989 | Frick et al. |
| 4,869,253 A | 9/1989 | Craig, Jr. et al. |
| 4,869,254 A | 9/1989 | Stone et al. |
| 4,883,353 A | 11/1989 | Hausman et al. |
| 4,892,101 A | 1/1990 | Cheung et al. |
| 4,907,594 A | 3/1990 | Muz |
| 4,911,167 A | 3/1990 | Corenman et al. |
| 4,927,264 A | 5/1990 | Shiga et al. |
| 4,928,692 A | 5/1990 | Goodman et al. |
| 4,934,372 A | 6/1990 | Corenman et al. |
| 4,948,248 A | 8/1990 | Lehman |
| 4,949,710 A | 8/1990 | Dorsett et al. |
| 4,955,379 A | 9/1990 | Hall |
| 4,956,867 A | 9/1990 | Zurek et al. |
| 4,958,638 A | 9/1990 | Sharpe et al. |
| 4,960,128 A | 10/1990 | Conlon et al. |
| 4,972,842 A | 11/1990 | Korten et al. |
| 5,025,791 A | 6/1991 | Niwa |
| 5,054,495 A | 10/1991 | Uemura et al. |
| 5,057,695 A | 10/1991 | Hirao et al. |
| 5,058,588 A | 10/1991 | Kaestle |
| 5,078,136 A | 1/1992 | Stone et al. |
| 5,190,038 A * | 3/1993 | Polson et al. ............... 600/330 |
| 5,246,002 A | 9/1993 | Prosser |
| 5,267,562 A | 12/1993 | Ukawa et al. |
| 5,273,036 A | 12/1993 | Kronberg et al. |
| 5,348,004 A | 9/1994 | Hollub |
| 5,351,685 A | 10/1994 | Potratz |
| 5,398,682 A | 3/1995 | Lynn |
| 5,431,170 A | 7/1995 | Mathews |
| 5,458,128 A | 10/1995 | Polanyi et al. |
| 5,467,778 A | 11/1995 | Catt et al. |
| RE35,122 E | 12/1995 | Corenman et al. |
| 5,479,922 A | 1/1996 | Reichl |
| 5,482,036 A | 1/1996 | Diab et al. |
| 5,485,847 A | 1/1996 | Baker, Jr. |
| 5,490,505 A | 2/1996 | Diab et al. |
| 5,494,032 A | 2/1996 | Robinson et al. |
| 5,503,148 A * | 4/1996 | Pologe et al. ............... 600/323 |
| 5,511,042 A | 4/1996 | O'Brien, Jr. |
| 5,524,631 A | 6/1996 | Zahorian et al. |
| 5,553,615 A | 9/1996 | Carim et al. |
| 5,575,284 A | 11/1996 | Athan et al. |
| 5,575,285 A | 11/1996 | Takanashi et al. |
| 5,588,439 A | 12/1996 | Hollub |
| 5,605,151 A | 2/1997 | Lynn |
| 5,632,272 A | 5/1997 | Diab et al. |
| 5,676,141 A | 10/1997 | Hollub |
| 5,685,299 A | 11/1997 | Diab et al. |
| 5,758,644 A | 6/1998 | Diab et al. |
| 5,769,785 A | 6/1998 | Diab et al. |
| 5,853,364 A | 12/1998 | Baker, Jr. et al. |
| 6,002,952 A | 12/1999 | Diab et al. |
| 6,067,462 A | 5/2000 | Diab et al. |
| 6,081,735 A | 6/2000 | Diab et al. |
| 6,157,850 A | 12/2000 | Diab et al. |
| 6,236,872 B1 | 5/2001 | Diab et al. |
| 6,430,525 B1 | 8/2002 | Weber et al. |
| 6,650,917 B1 | 11/2003 | Diab et al. |
| 6,699,194 B1 | 3/2004 | Diab et al. |
| 6,745,060 B1 | 6/2004 | Diab et al. |
| 6,836,679 B1 | 12/2004 | Baker, Jr. et al. |

FOREIGN PATENT DOCUMENTS

| | | |
|---|---|---|
| EP | 0341 327 A1 | 11/1988 |
| GB | 2 166 326 | 4/1986 |
| GB | 2 235 288 | 2/1991 |
| SU | 1674798 A1 | 9/1991 |
| WO | WO 92/15955 | 9/1992 |

OTHER PUBLICATIONS

Rabiner et al., "Theory and Application of Digital Signal Processing," p. 260 (1975).

Mook et al., *Cardiovascular Research*, 13:233-237 (1979).

Nehorai, A., "A Minimal Parameter Adaptive Notch Filter With Constrained Poles and Zeros," *IEEE Transactions on Acoustics Speech, and Signal Processing*, ASSP-33(4):9083-996 (1985).

Nehorai, A., et al., "Adaptive Comb Filtering for Harmonic Signal Enhancement," *IEEE Transactions on Acoustics, Speech, and Signal Processing*, ASSP-14 (5):1124-1138 (1986).

Gilbert Strang, *Introduction to Applied Mathematics*, Wellesley Cambridge Press, Wellesley, Mass. (1986), pp. 148-152.

Brown, "Evaluation of Pulse Oximeters Using Theoretical Models and Experimental Studies," Cover page-p. 2 (1987).

Neuman, "Pulse Oximetry: Physical Principles, technical Realization and Present Limitations," *Continuous Transcutaneous Monitoring*, pp. 135-144 (1987).

Jinzheng et al., "Digital Processing of High-Resolution electrocardiograms-Detection of His-Purkinje Activity from the Body Surface," *Biomed. Technik*, 33(10):224-230 (1988).

Chen et al., "Adaptive Syustem for Processing of electrogastric Signals," *IEEE Engineering in Medicine & Biology Society*, 11th Annual International conference, pp. 698-699 (1989).

Klimasauskas, "N eural Nets and Noise Filtering," *Dr. Dobb's Journal*, 14(1):32-48 (1989).

Severinghaus, "Pulse Oximetry Uses and Limitations," ASA Convention in New Orleans, LA (1989).

Harris et al., "D igital Signal processing with Efficient Polyphase Recursie All-Pass Filters," *International Conf. on Signal Processing*, Florence, Italy (1991).

Varanini et al., "A Two-Channel Adaptive Filtering Approach for Recogniation of the QRS Morphology," Computers in Cardiology, pp. 11-144 (1991).

Robert Grover Brown and Patrick Y.C. Hwang, *Introduction to Random Signals and Applied Kalman Filtering* (2nd Ed.), John Wiley & Sons, Inc., New York (1992), pp. 231-232, 261.

Hendry, S.D., "Computation of Harmonic Comb Filter Weights," *IEEE Transactions on Signal Processing*, 41(4): 1677-1680 (1993).

Testimony of Mohammed Diab, Testimony of Jack Goldberg, Reporter's Transcript of Proceedings, Morning Session, Feb. 24, 2004, pp. 626-710, US District Court, central District of California, No. CV 00 6506-MRP, Los Angeles, California.

Testimony of Jack Goldberg, Reporter's Transcript of Proceedings, Afternoon session, Feb. 24, 2004, pp. 711-806, US District Court, Central District of California, No. CV 00 6506-MRP, Los Angeles, California.

Testimony of Jack Goldberg, Reporter's Transcript of Proceedings, Morning session, Feb. 25, 2004, pp. 807-826, US District Court, Central District of California, No. CV 00 6506-MRP, Los Angeles, California.

Testimony of James Edward, Corenman, Testimony of Clark Raymond Baker, Jr., Testimony of Robert Thomas Stone, Reporter's Transcript of Proceedings, Afternoon session, Mar. 3, 2004, pp. 1696-1795, US. District Court, Central District of California, No. CV 00 6506-MRP, Los Angeles, California.

Testimony of Robert Thomas Stone, Reporter's Transcript of Proceedings, Morning session, Mar. 4, 2004, pp. 1796-1884, US District Court, Central District of California, No. CV 00 6506-MRP, Los Angeles, California.

*Mallinckrodt Inc. and Nellcor Puritan Bennett, Inc. v. Masimo Corp. and Ivy Biomedical Systems, Inc.,* Memorandum of Decision and order Re Power-Trial Motions entered Jul. 14, 2004.

*Mallinckrodt Inc. and Nellcor Puritan Bennett, Inc. v. Masimo Corp. and Ivy Biomedical Systems, Inc.,* Final Judgment entered Aug. 6, 2004.

FastSat™ Whitepaper by Masimo Corporation (2 pages)—undated.

Cohen, *Biomedical Signal Processing*, vol. 1, pp. 152-159.

Joint Exhibits: JTX-5009, JTX-5010, JTX-5013, JTJ-5014, TJX-5015, JTX-5017, JTX-5021, US District Court, Central District of California, No. CV 00 6506-MRP, Los Angeles, California.

Wahr, Joyce A., et al,, "Pulse Oximetry," *Respiratory Care Clinics of North America, Blood Gas Measurements*, 1:1 (Sep. 1995), pp. 77-105.

* cited by examiner

PULSE OXIMETER SENSOR OFF DETECTOR

RELATED APPLICATION DATA

The present application is a continuation of application Ser. No. 09/876,004, filed Jun. 6, 2001, now U.S. Pat. No. 6,721,584, which is a continuation of application Ser. No. 09/435,144, filed Nov. 5, 1999, now abandoned, which is a continuation of application Ser. No. 09/137,479, filed Aug. 20, 1998, now U.S. Pat. No. 6,083,172, which is a continuation of application Ser. No. 08/660,510, filed Jun. 7, 1996, now U.S. Pat. No. 5,853,364, which is a non-provisional utility patent application based on Provisional Patent Application No. 60/000,195 filed on Jun. 14, 1995, from which the present application claims priority.

BACKGROUND OF THE INVENTION

The present invention relates to a method and apparatus which uses model-based adaptive filtering techniques to estimate physiological parameters. More specifically, the invention employs Kalman filtering techniques in pulse oximetry to estimate the oxygen saturation of hemoglobin in arterial blood.

Pulse oximeters typically measure and display various blood flow characteristics including but not limited to the oxygen saturation of hemoglobin in arterial blood. Oximeters pass light through blood perfused tissue such as a finger or an ear, and photoelectrically sense the absorption of light in the tissue. The amount of light absorbed is then used to calculate the amount of the blood constituent (e.g., oxyhemoglobin) being measured.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption.

When the measured blood parameter is the oxygen saturation of hemoglobin, a convenient starting point assumes a saturation calculation based on Lambert-Beer's law. The following notation will be used herein:

$$I(\lambda, t) = I_o(\lambda)\exp(-(s\beta_o(\lambda)+(1-s)\beta_r(\lambda))l(t)) \quad (1)$$

where:
 $\lambda$=wavelength;
 t=time;
 I=intensity of light detected;
 $I_o$=intensity of light transmitted;
 s=oxygen saturation;
 $\beta_o$, $\beta_r$=empirically derived absorption coefficients; and
 l(t)=a combination of concentration and path length from emitter to detector as a function of time.

The traditional approach measures light absorption at two wavelengths, e.g., red and infrared (IR), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \cong \log I(\lambda, t_2) - \log I(\lambda, t_1)$$

Using log A−log B=log A/B, $$\frac{d\log I(\lambda, t)}{dt} \cong \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \cong \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} \equiv R \quad (5)$$

where R represents the "ratio of ratios."

Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5) note that R can be calculated using two points (e.g., plethysmograph maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \cong \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (7)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R$$

Now define

Then describes a cluster of points whose slope of y versus x will give R.

$$x(t)=[I(t_2,\lambda_{IR})-I(t_1,\lambda_{IR})]I(t_1,\lambda_R)$$

$$y(t)=[I(t_2,\lambda_R)-I(t_1,\lambda_R)]I(t_1,\lambda_{IR}) \quad (8)$$

$$y(t)=Rx(t)$$

The optical signal through the tissue can be degraded by both noise and motion artifact. One source of noise is ambient light which reaches the light detector. Another source of noise is electromagnetic coupling from other electronic instruments. Motion of the patient also introduces noise and affects the signal. For example, the contact between the detector and the skin, or the emitter and the skin, can be temporarily disrupted when motion causes either to move away from the skin. In addition, since blood is a fluid, it responds differently than the surrounding tissue to inertial effects, thus resulting in momentary changes in volume at the point to which the oximeter probe is attached.

Motion artifact can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site.

In one oximeter system described in U.S. Pat. No. 5,025,791, an accelerometer is used to detect motion. When motion is detected, readings influenced by motion are either eliminated or indicated as being corrupted. In a typical oximeter, measurements taken at the peaks and valleys of the blood pulse signal are used to calculate the desired characteristic. Motion can cause a false peak, resulting in a measurement having an inaccurate value and one which is recorded at the wrong time. In U.S. Pat. No. 4,802,486, assigned to Nellcor, the assignee of the present invention, the entire disclosure of which is incorporated herein by reference, an EKG signal is monitored and correlated to the oximeter reading to provide synchronization to limit the effect of noise and motion artifact pulses on the oximeter readings. This reduces the chances of the oximeter locking onto a periodic motion signal. Still other systems, such as the one described in U.S. Pat. No. 5,078,136, assigned to Nellcor, the entire disclosure of which is incorporated herein by reference, use signal processing in an attempt to limit the effect of noise and motion artifact. The '136 patent, for instance, uses linear interpolation and rate of change techniques to analyze the oximeter signal.

Each of the above-described techniques for compensating for motion artifact has its own limitations and drawbacks. It is therefore desirable that a pulse oximetry system be designed which more effectively and accurately reports blood-oxygen levels during periods of motion.

SUMMARY OF THE INVENTION

According to the present invention, a method and apparatus are provided for reducing the effects of motion artifact and noise on a system for measuring physiological parameters, such as, for example, a pulse oximeter. The method and apparatus of the invention take into account the physical limitations on various physiological parameters being monitored when weighting and averaging a series of samples or measurements. Varying weights are assigned different measurements. Optionally, measurements are rejected if unduly corrupt. The averaging period is also adjusted according to the reliability of the measurements. More specifically, a general class of filters is employed in processing the measurements. The filters use mathematical models which describe how the physiological parameters change in time, and how these parameters relate to measurement in a noisy environment. The filters adaptively modify a set of averaging weights and averaging times to optimally estimate the physiological parameters.

In a specific embodiment, the method and apparatus of the present invention are applied to a pulse oximeter which is used to measure the oxygen saturation of hemoglobin in arterial blood. The system takes the natural logarithm of optical oximetry data and then bandpass filters the data to get absorption-like data. The bandpass filter strongly attenuates data below 0.5 Hz and above 10 Hz in an attempt to remove as much out-of-band noise as possible. This filtered data is then processed through two algorithms: a rate calculator and a saturation calculator.

The system calculates the heart rate of the patient one of three ways using the oximetry data. An adaptive comb filter (ACF) is employed to track the slowly varying heart rate. The tracking of the heart rate by the ACF is quite robust through noisy environments, however, the ACF is not a good heart rate finder. As a result, the system periodically calculates the power spectrum of one of the wavelengths and uses it to find and/or verify the heart rate. In cases of arrhythmia or suddenly changing heart rates, the system employs a pattern matching technique that recognizes sequences of crests and troughs in the data and calculates an average heart rate period over a set number of samples.

The system then employs the calculated heart rate to digitally comb filter the data so that only the energy at integer multiples of the heart rate are allowed through the filter. The comb filter frequency varies as the heart rate varies, attenuating motion energy not at the heart rate or multiples thereof. To remove noise energy at integer multiples of the heart rate, the system adaptively signal averages full cycles of past plethysmographs, i.e., pleths, using a Kalman filter to limit the rate of change in the pleth shape or size.

The system then calculates two saturations, one with the pleth cycle data which has been comb filtered as described above, and one with raw data from the output of the band pass filter. Both saturations are calculated using time based signals and using an adaptive Kalman filter which continuously weights all data according to an estimate of the current noise, and limits the rate of change of saturation to a defined limit (currently 1.3 saturation points per second). Data points that result in a saturation calculation (prior to weighting and averaging) which is obviously not physiologically possible (e.g., negative saturation, or a saturation greater than 100%) are deemed invalid and are not used and are rejected in an "outlier rejection" step in both saturation calculations. The system then arbitrates between the two saturation values based on rules described below to determine the best saturation. For example, the arbitration may be based on such factors as the noise level or the age of the saturation value. The best saturation may also be a weighted average of the different saturation values.

According to a specific embodiment of the invention, a method for reducing noise effects in a system for measuring a physiological parameter is provided. A plurality of measurements is generated corresponding to at least one wavelength of electromagnetic energy transmitted through living tissue. Selected measurements are compared with at least one expected measurement characteristic. A variable weight is assigned to each of the selected measurements based on the comparison, thereby generating a plurality of differently weighted measurements for each wavelength. A first number of weighted measurements is averaged to obtain a filtered measurement, the first number varying according to the manner in which weights are assigned to a plurality of successive weighted measurements. A plurality of filtered measurements are thus generated for each wavelength. The filtered measurements for each wavelength are then combined and calculations resulting therefrom are adaptively filtered using variable weights based on comparing the calculations to an expected calculation. A second number of the weighted calculations are averaged to obtain a filtered calculation, the second number varying according to the manner in which weights are assigned to a plurality of successive weighted calculations.

A further understanding of the nature and advantages of the present invention may be realized by reference to the remaining portions of the specification and the drawings.

DESCRIPTION OF THE PREFERRED EMBODIMENT

Figure 1A:
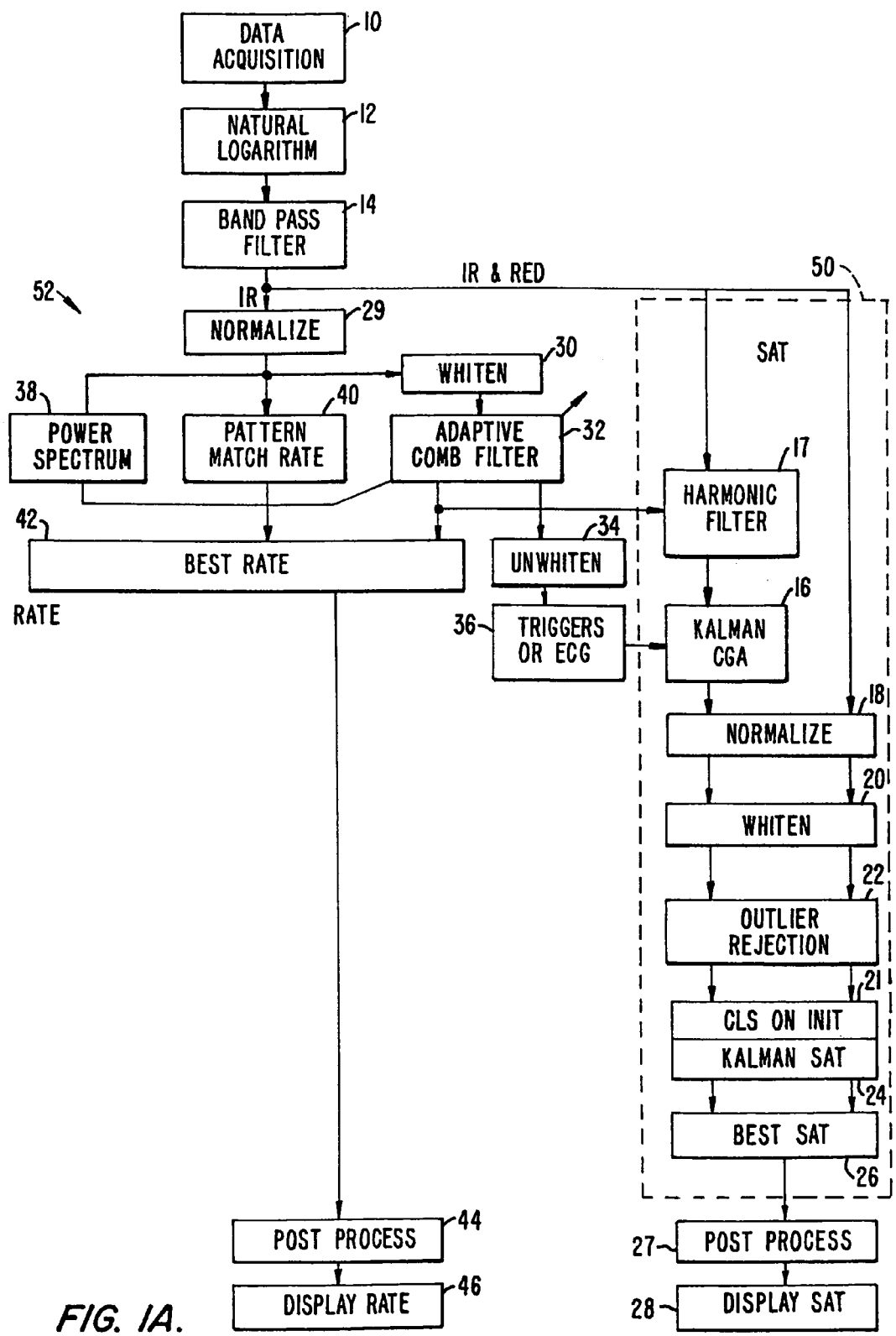
FIGS. 1a and 1b are block diagrams illustrating the data flow in a pulse oximetry system designed according to two specific embodiments of the invention.

FIG. 1a shows the flow of data according to one embodiment of the present invention. A separate platform collects the oximetry data (step 10) and passes it to processors 50 and 52 of the present invention. A preferred platform is described in U.S. Pat. No. 5,348,004 assigned to Nellcor, the entire disclosure of which is incorporated herein by reference. The data is first pre-processed (steps 12 and 14), and is then passed to a saturation calculation algorithm (box 50). The algorithm described herein employs an improved Kalman filter method (step 24). It will be understood that other saturation calculation techniques may be employed. The pulse rate calculation method (box 52) and a cardiac gated averaging technique also using a Kalman filter (step 16) are discussed below.

Figure 2:
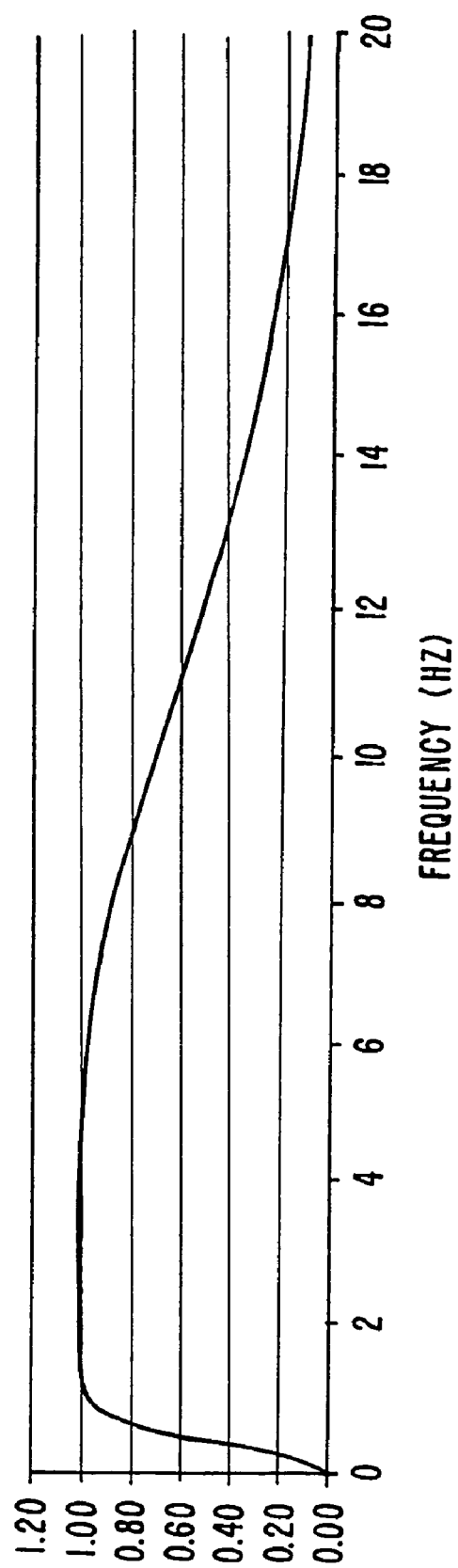
FIG. 2 shows the frequency response of an infinite impulse response (IIR) filter employed by a specific embodiment of the invention.

According to a preferred embodiment, the processing technique employs the following pre-processing. The natural logarithm of the IR and Red wavelength data is taken (step 12), and then the data is band pass filtered with an infinite impulse response (IIR) filter that has a high pass cutoff frequency at 0.5 Hz, i.e., 30 beats per minute, and a low pass rolloff from 10 to 20 Hz (step 14). FIG. 2 shows the frequency response of an IIR filter employed by a specific embodiment of the invention.

After the oximetry data has been filtered, it is processed by a saturation calculation algorithm (box 50). According to a preferred embodiment of the invention depicted in FIG. 1a, two saturation values are calculated in parallel by saturation calculator 50. One saturation value is calculated using a harmonic filter 17 and a Kalman-filter-based cardiac gated averaging (CGA) technique (step 16) (described below) to obtain a more reliable data stream. Kalman CGA 16 is gated by triggers based on the pulse rate which are supplied by pulse rate calculator 52. In a specific embodiment, the data is put through a harmonic filter (step 17) before it is averaged in step 16. Harmonic filter 17 digitally filters the IR and red waveforms such that only energy at integer multiples of the heart rate is allowed through the filter. The response of harmonic filter 17 varies with the heart rate which is supplied by pulse rate calculator 52 to attenuate motion and noise energy not at the heart rate. In one embodiment, only one of the IR and red waveforms is filtered by harmonic filter 17. In this embodiment, the subsequent filtering by Kalman CGA 16 and/or the saturation calculation algorithm described below applies the same weighting and averaging to both the IR and red data streams on the basis of the single filtered data stream.

Both saturation values are calculated in the following manner. The data pulses (either directly from the band pass filter or from steps 16 and 17) are normalized (step 18) and then "whitened" (step 20). Normalizing downweights large pulse amplitudes so that each pulse has roughly the same average amplitude. Normalizing step 18 assumes that from one sample to the next, noise energy should look substantially the same statistically. As a result, samples exhibiting large amounts of noise are down weighted, thus de-emphasizing outliers. Whitening step 20 involves taking the derivative of the normalized data, thereby emphasizing the higher harmonics of the pleth so that its energy is more evenly distributed between them. Data points resulting in an impossible saturation calculation are rejected (step 22) and the resulting data are used to calculate the saturation values using a Kalman filter technique described below (step 24). The best saturation value is then chosen (step 26) according to confidence levels associated with each, and, after some post processing (step 27), the saturation value is output to the display (step 28). Post processing 27, which will be discussed in greater detail below, uses available metrics with regard to the saturation value to determine its reliability and determine whether and how it is to be displayed. In specific preferred embodiments of the present invention, the initial saturation value calculated by each calculation path in saturation calculator 50 may be calculated by the well known classic least squares (CLS) technique as indicated by step 21. The use of this technique occurs on initialization of saturation calculator 50 only.

The pulse or heart rate is calculated in pulse rate calculator 52 in the following manner. After the pre-processing described above, data from one channel, e.g., the IR channel, are normalized (step 29) by the downweighting of data corresponding to large pulse amplitudes so that each pulse has roughly the same average amplitude. The data are then sent to two different algorithms for calculation of the patient's pulse rate. According to one algorithm, the derivative of the data is taken (step 30) as described above, and the fundamental frequency of the pulse rate is tracked using an adaptive comb filter (ACF) 32 as discussed below. ACF 32 supplies its pulse rate directly to harmonic filter 17 as described above. ACF 32 also provides the trigger for Kalman CGA 16 after the data is unwhitened by integration (step 34) and the triggers for Kalman CGA are generated (step 36). Alternatively, the triggers for Kalman CGA 16 may be derived from, for example, an ECG waveform. ACF 32 is a robust pulse rate tracker, but not a good pulse rate finder. Therefore, the frequency power spectrum of the normalized data is calculated periodically (step 38) to determine whether ACF 32 is tracking the fundamental rather than a super- or subharmonic of the pulse rate.

The normalized data is also supplied to a pattern matching algorithm 40 which recognizes sequences of crests and troughs in the data and calculates an average period of the pleth over a set number of samples. This algorithm is preferably used primarily to track the pulse rate for an arrhythmic pulse rate during periods where no motion is detected. A best rate algorithm 42 then arbitrates between the pulse rates calculated by ACF 32 (as updated by frequency power spectrum 38) and pattern matching algorithm 40 using confidence levels associated with each, which are based on various metrics. After post processing (step 44), the pulse rate is output to the display (step 46). As with saturation calculator 50, post processing 44 uses available metrics to determine the reliability of the pulse rate and to determine whether and how it is to be displayed.

Figure 1B:
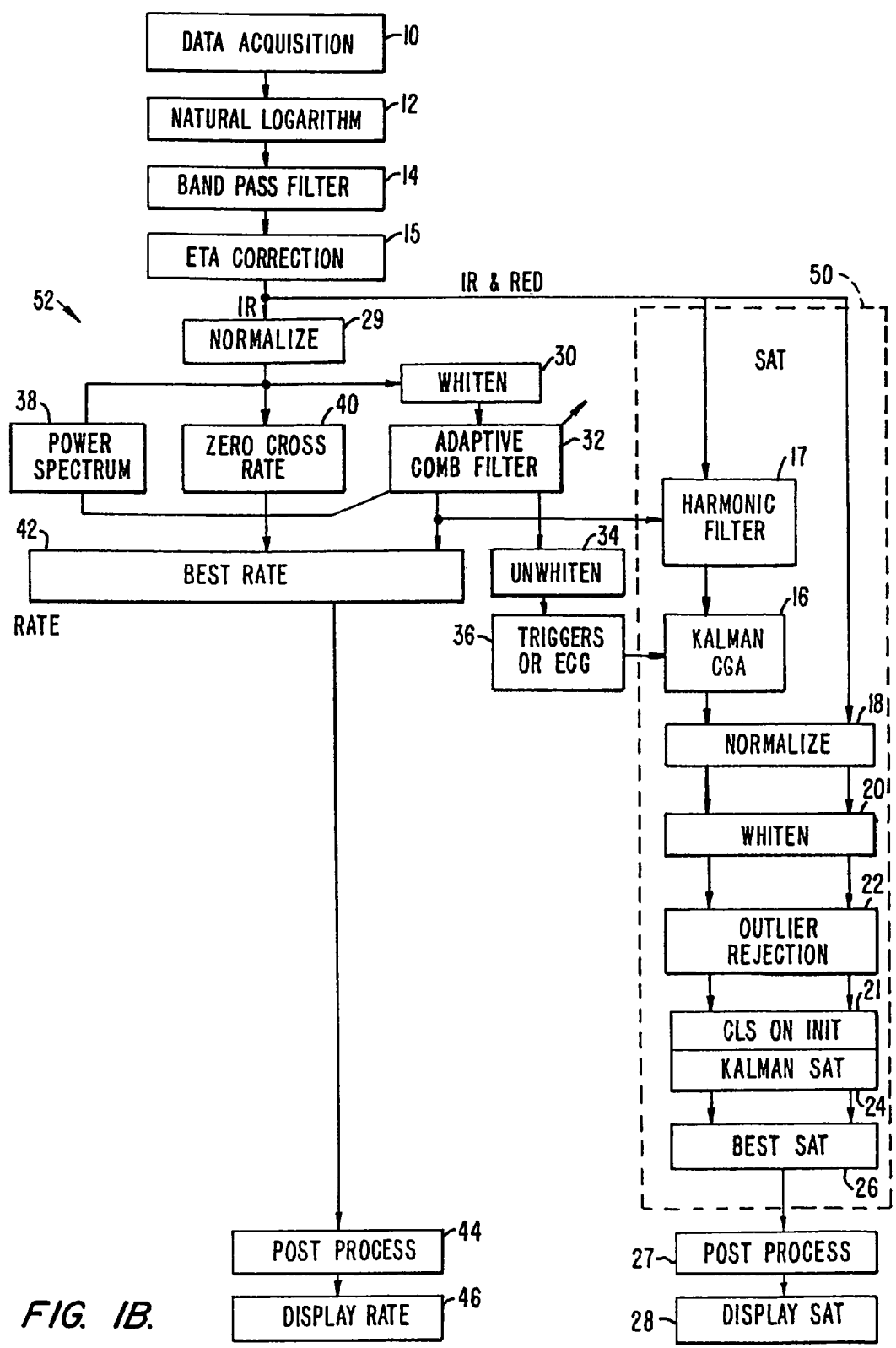

FIG. 1*b* shows the flow of data according to a second embodiment of the present invention. The system operates the same as the system of FIG. 1*a* except that after the data is band pass filtered by IIR filter 14, it undergoes an additional processing step in eta correction processor 15 before it is sent to either saturation calculation algorithm 50 or pulse rate calculation algorithm 52. Like other aspects of the present invention already described, eta correction processor 15 serves to reduce the effects of motion and other noise artifact. The operation of eta correction processor 15 is based on an analysis of the signal intensity received for the different wavelengths, without separately measuring the motion signal for each wavelength, without providing feedback to cancel the motion signal, and without attempting to mathematically eliminate the motion signal individually for each wavelength. Instead, processor 15 mathematically recognizes the presence of the motion signal and recognizes a few key characteristics of the motion signal. First, although the magnitude of the effect of motion on the signal intensity for each wavelength will be different, the change in the logarithm of the motion component will be approximately the same (for signals obtained at approximately the same time). This allows the motion component to be cancelled out in a ratiometric equation. Second, it is assumed that the blood pulse signal is not affected by motion. This second assumption is more of an approximation, since the blood pulse signal is somewhat affected by motion, which can actually change the blood volume characteristics at any point in the patient. Eta correction processor 15 recognizes that the intensity signal for each of the wavelengths includes a time-varying motion term, and that this time-varying motion term is proportional for each of the wavelengths. In addition, each wavelength signal occurs close enough in time with one another that the motion should not vary noticeably, and can be assumed to be the same for each signal. The output from eta correction processor 15 is an IR or red signal which has significantly less motion noise than the signals fed into processor 15. If the data include information from a third wavelength, the output of processor 15 is both an IR signal and a red: signal depleted of motion noise. A more detailed description of the operation of eta correction processor 15 is described in a commonly assigned, copending U.S. patent application Ser. No. 08/490, 315 for METHOD AND APPARATUS FOR REMOVING ARTIFACT AND NOISE FROM PULSE OXIMETRY, filed Jun. 14, 1995, the entire disclosure of which is incorporated herein by reference.

The method for calculation of blood oxygen saturation (step 24) described below uses a Kalman filter. The method first transforms the pre-processed data into quantities corresponding to the oxyhemoglobin and total hemoglobin concentrations using appropriate extinction coefficients. The instantaneous ratio of these two transformed quantities gives the saturation. It will be understood from the equation immediately following equation (4) above that the instantaneous saturation value may be calculated directly by using the extinction coefficients, or from the ratio of ratios as shown in the equation immediately following equation (5). According to a preferred embodiment, the method does not search for maxima or minima like a pulse searching algorithm (although maxima or minima could be used and Kalman filtered if desired). Using instantaneous ratios (i.e., a time based algorithm) rather than maxima/minima ratios (i.e., an event based algorithm) keeps the code from being event driven and having to qualify data as it arrives. Thus, the preferred method of the present invention is simpler to implement than a pulse-searching event-based saturation calculation algorithm.

Figure 3:
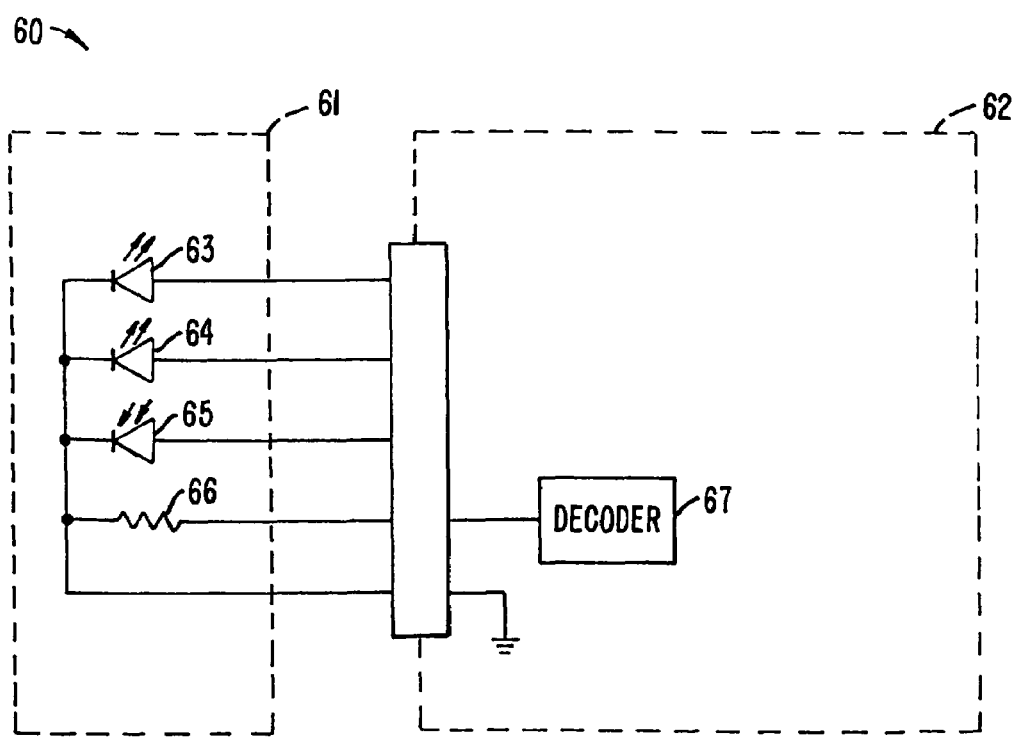
FIG. 3 shows a sensor/oximeter combination for use with the present invention in which the transmission characteristics of the sensor are identified by a calibration resistor.

The extinction coefficients are determined with reference to the wavelength or wavelengths being transmitted by the LEDs in the particular sensor attached to the patient. In a preferred embodiment, the sensor includes a means for generating a signal which corresponds to at least one of the wavelengths being transmitted by the sensor's LEDs. The oximeter monitor receives the signal and determines the proper extinction coefficients based on the wavelength or wavelengths indicated by the signal. This avoids the need to recalibrate an oximeter to match the transmission characteristics of a particular probe. In a preferred embodiment, the means for generating the signal is an electrical impedance element such as, for example, a resistor, the value of which corresponds to the wavelengths of the LEDs. A preferred embodiment of a sensor/oximeter combination is shown in FIG. 3. Oximetry system 60 includes a sensor 61 and an oximeter monitor 62. Sensor 61 includes LEDs 63 and 64 typically having wavelength emission characteristics in the infrared and red ranges of the spectrum, respectively. Photodiode sensor 65 receives the light transmitted by LEDs 63 and 64. Resistor 66 (or a similar electrical impedance reference) is chosen to correspond to a specific wavelength or combination of wavelengths as specified by a table relating impedance values to wavelengths. Once decoding means 67 determines the impedance value of resistor 66, appropriate extinction coefficients are generated which correspond to the transmission characteristics of the particular sensor 61. Thus, the oximeter may be used with a variety of sensors having LEDs which emit varying wavelengths of light without recalibration.

Sensor 61 may be detachably coupled to oximeter monitor 62 via connector 68. An example of such a sensor/oximeter combination is described in commonly assigned U.S. Pat. No. 4,621,643 for CALIBRATED OPTICAL OXIMETER PROBE, issued on Nov. 11, 1986; U.S. Pat. No. 4,700,708 for CALIBRATED OPTICAL OXIMETER PROBE, issued on Oct. 20, 1987; and U.S. Pat. No. 4,770,179 for CALIBRATED OPTICAL OXIMETER PROBE, issued on Sep. 13, 1988, the entire disclosures of which are incorporated herein by reference.

The Kalman Filter Solution

Kalman filtering allows one to fit parameters in a least squares sense when these parameters are varying in time. Traditionally one might employ a classical least squares (CLS) approach with low-pass filtering or averaging of the estimated quantity. Essentially Kalman filtering does the same thing, but the Kalman filter calculates the optimal amount of averaging. One embodiment employs a Kalman filter algorithm derived by R. G. Brown and P. Y. C. Hwang in *Introduction to Random Signals and Applied Kalman Filtering* (1992), the disclosure of which is incorporated herein by reference. A simplified general Kalman filter is described below.

In this example, an estimate of the data average is made as the data are being measured. The measured data also has a gain H to be removed. The k-th measurement is $z_k$ and the k-th estimate of the average is $x_k$. The first estimate of the average is just the measurement $$x_1 = \frac{z_1}{H}$$

After the second measurement the estimate becomes $$x_2 = \frac{z_1 + z_2}{2H}$$

after the third measurement $$x_3 = \frac{z_1 + z_2 + z_3}{3H}$$

This may be continued, but after a while becomes inefficient because of the need to store all of the measurements, constantly re-add them all, and divide by the gain and the number of measurements. A more efficient solution uses only the last estimate of the average and the current measurement. With this solution, after the first measurement, the estimate is still $$x_1 = \frac{z_1}{H}$$

However, after the second measurement the estimate becomes $$x_2 = \frac{x_1}{2} + \frac{z_2}{2H}$$

and after the third measurement $$x_3 = \frac{2x_2}{3} + \frac{z_3}{3H}$$

This approach may be generalized to $$x_k = \left(\frac{k-1}{k}\right)x_{k-1} + \frac{1}{kH}z_k$$
$$= x_{k-1} + \frac{1}{kH}(z_k - Hx_{k-1})$$
$$= x_{k-1} + K(z_k - Hx_{k-1})$$

where we have used K to simplify the equation notation. The Kalman filter uses the same ideas with some extensions: the Kalman filter optimally filters noise, and the parameter being estimated can vary in time.

A simplified Kalman filter employed in one embodiment of the present invention will now be described. The parameter to be estimated (for example, saturation) is x which varies in time in some predictable way. If the value of x is known at some sample in time, then in the next sample, x may be expected to have little or no variation from the previous value. Q is the variance of this difference. The parameter x is not measured directly. What is actually measured is a parameter z which equals x times a constant H plus measurement noise. R is the variance of this measurement noise. Rewriting these $$x_k = x_{k-1} + n_k^Q$$

$$z_k = H_k x_k + n_k^R$$

The ability to estimate the value of x knowing z and the last estimate of x is related to the two noises quantified by R and Q. The Kalman filter quantifies the two noises in a parameter called the estimation error, P. The Kalman filter also uses an intermediate term called the Kalman gain, K. $P^{o-1}$ is initialized with a value of zero. Then at each new data point k, the following steps are performed:

$$P_k^{-1} = P_{k-1}^{-1} + H_k^2 R_k^{-1}$$

$$K_k = P_k H_k R_k^{-1}$$

$$x_k = x_{k-1} + K_k(z_k - H_k x_{k-1})$$

$$P_{k+1} = P_k + Q_k$$

Notice how the estimate $x_k$ looks like the sample averaging example.

With the Kalman filter, the saturation is allowed to vary, and the model is separated into two parts. The first part is $$v_k = u_k s_k + n_k^R$$

That is, the ratio of the transformed pre-processed data is the saturation value except for measurement noise. The spread of the data gives a real-time measurement of the noise variance. The second part says that on average saturation does not change in time, but if it does change the standard deviation of the change is some constant, $Q^{1/2}$ (1.3 saturation points per second in one embodiment). That is, the second equation is $$s_k = s_{k-1} + n_k^Q$$

This second equation gives the Kalman filter the ability to recognize that if saturation changes by 10 points in two seconds, for example, it must be due to measurement noise. The Kalman filter then averages the calculated saturation more with previous values to bring the change more in line with what is expected from physiology. In contrast, if the change is within bounds the Kalman filter will average very little.

The value of R is estimated from the difference between v and us over the last N points, where the user specifies the value N. In one embodiment, the Kalman model for saturation also gives less weight to the smaller portions of a pulse, more weight to the larger portions, and adds a small incremental value to the actual variance to represent the error inherent in the measurement system (e.g., hardware noise).

In another preferred embodiment, a Kalman filter limits the changes to the time derivative of saturation. The equations for this filter say that the expected value of the time derivative of saturation should statistically be unchanged with time.

$$\frac{dx_k}{dt} = \frac{dx_{k-1}}{dt} + n_k^Q$$

$$\frac{dz_k}{dt} = \frac{dx_k}{dt} + n_k^P$$

where z is the estimate of saturation from the first Kalman filter, and x is the estimate of saturation after limiting its time derivative. In this embodiment, the parameter $n^Q$ is preferred to be chosen to correspond to 0.2 saturation points per second per second, and $n^P$ is estimated from the data. In the general form of the Kalman filter, these two separate filters could be combined into one filter. By separating them, the need to use matrix algebra is eliminated and each Kalman filter is able to be tested separately.

The measurement noise is estimated by centering a window around the data values being used. This centering gives a more accurate estimate of the noise, but delays the output of the Kalman filter by half the window length. A one second window is preferred under the belief that the filter can respond quickly to motion coming and going, and the one-half second delay in saturation estimation is not clinically significant.

Figure 4:
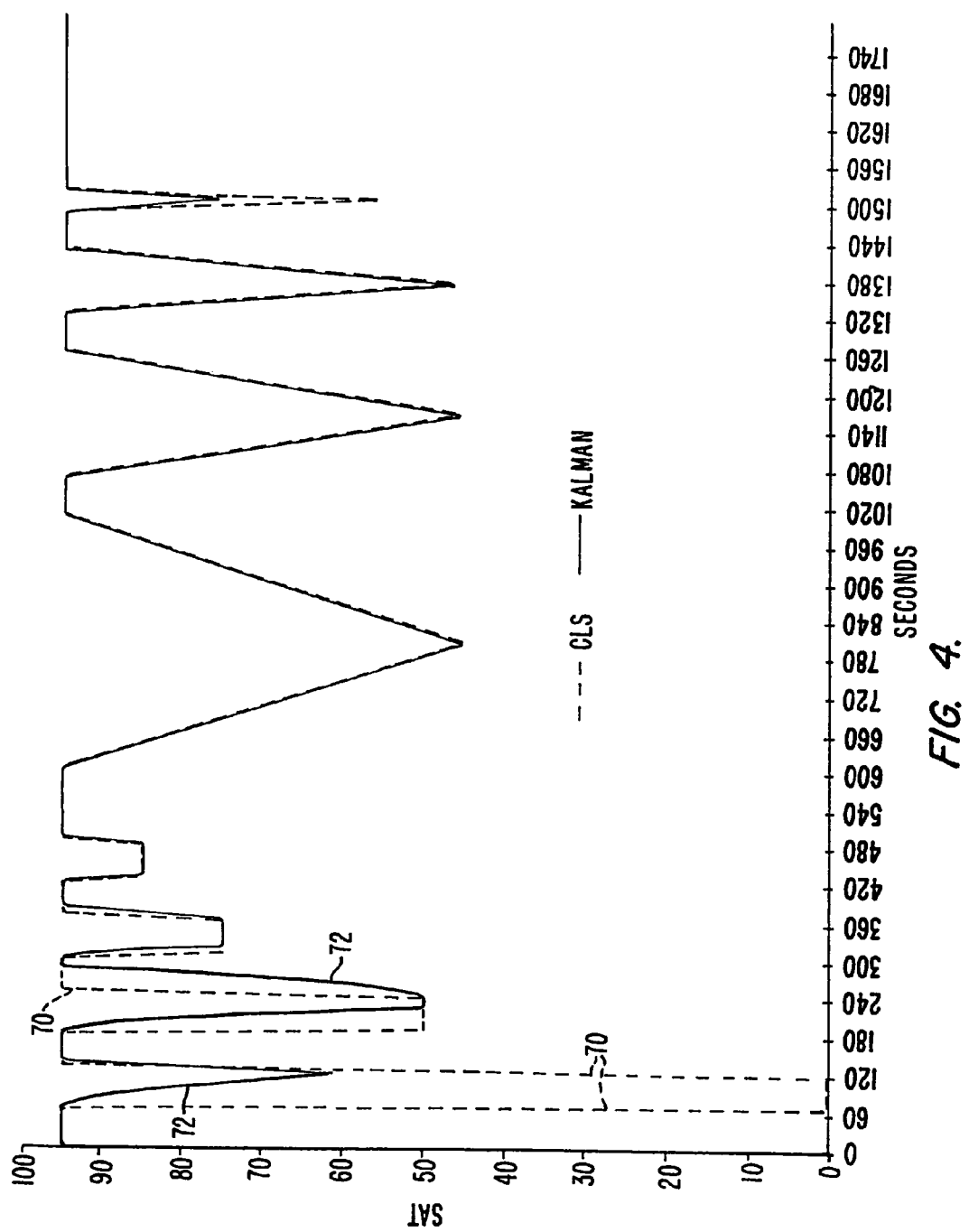
FIG. 4 is a graph comparing the performance of a classic least squares algorithm to that of the Kalman algorithm.

The Kalman filter employed by the present invention behaves in a very robust manner. Although motion can fool the Kalman filter, in most instances Kalman filtering results in the calculated saturation remaining closer to truth much longer than the CLS method and other known prior art methods. FIG. 4 compares the response of a saturation calculation algorithm employing the classic least squares (CLS) solution (70) and the Kalman filter (72) saturation algorithm to several artificial changes in saturation which occur at physiologically unbelievable rates. For rapid changes, the Kalman filter slows down the response to a specified rate, whereas the CLS algorithm quickly changes saturation, going to a value which is clearly erroneous in view of physiological realities. For slow changes, both algorithms track the same saturation change.

Kalman Cardiac Gated Averaging

A further feature of the present invention is the Kalman CGA processor 16 which again uses Kalman filter theory. Preferably, Kalman CGA 16 is used in series with Kalman saturation. The data used is after the preprocessing step 17 described above. The Kalman CGA processor 16 optimally averages successive pleth pulses or waveforms to create an optimally filtered pleth waveform. The first equation following says that the measured pleth shape should equal the averaged pleth wave shape except for measurement noise.

$$z_k = x_k + n_k^Q$$

The value of Q is estimated from the data. The next equation following says the new pulse cannot be more than some percentage (10% or 20% in two preferred embodiments) different from the averaged pleth pulse.

$$x_k = x_{k-N} + n_k^P$$

Figure 5:
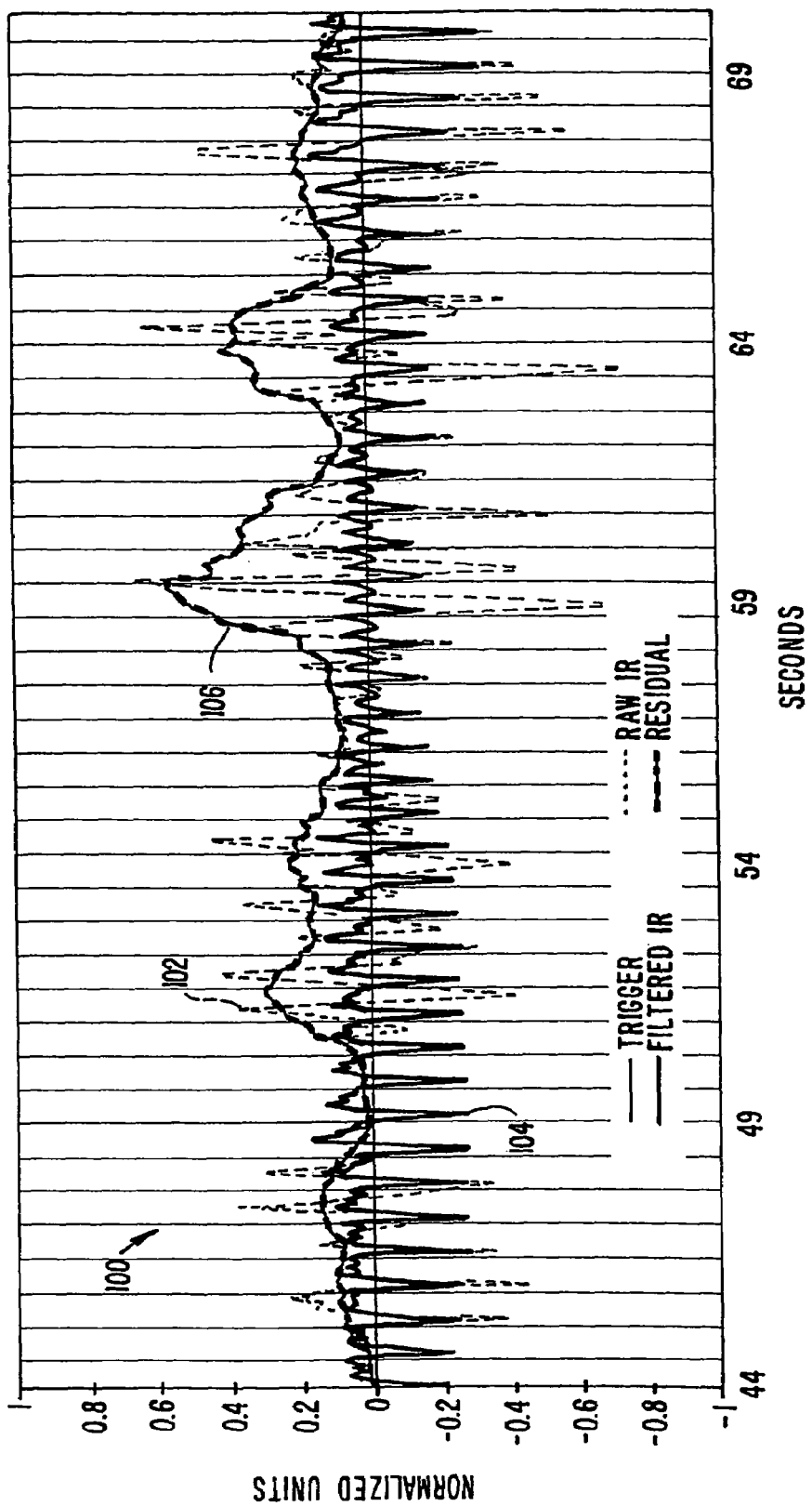
FIG. 5 is a graph comparing the inputs and outputs of the Kalman cardiac gated averaging filter.
Figure 6:
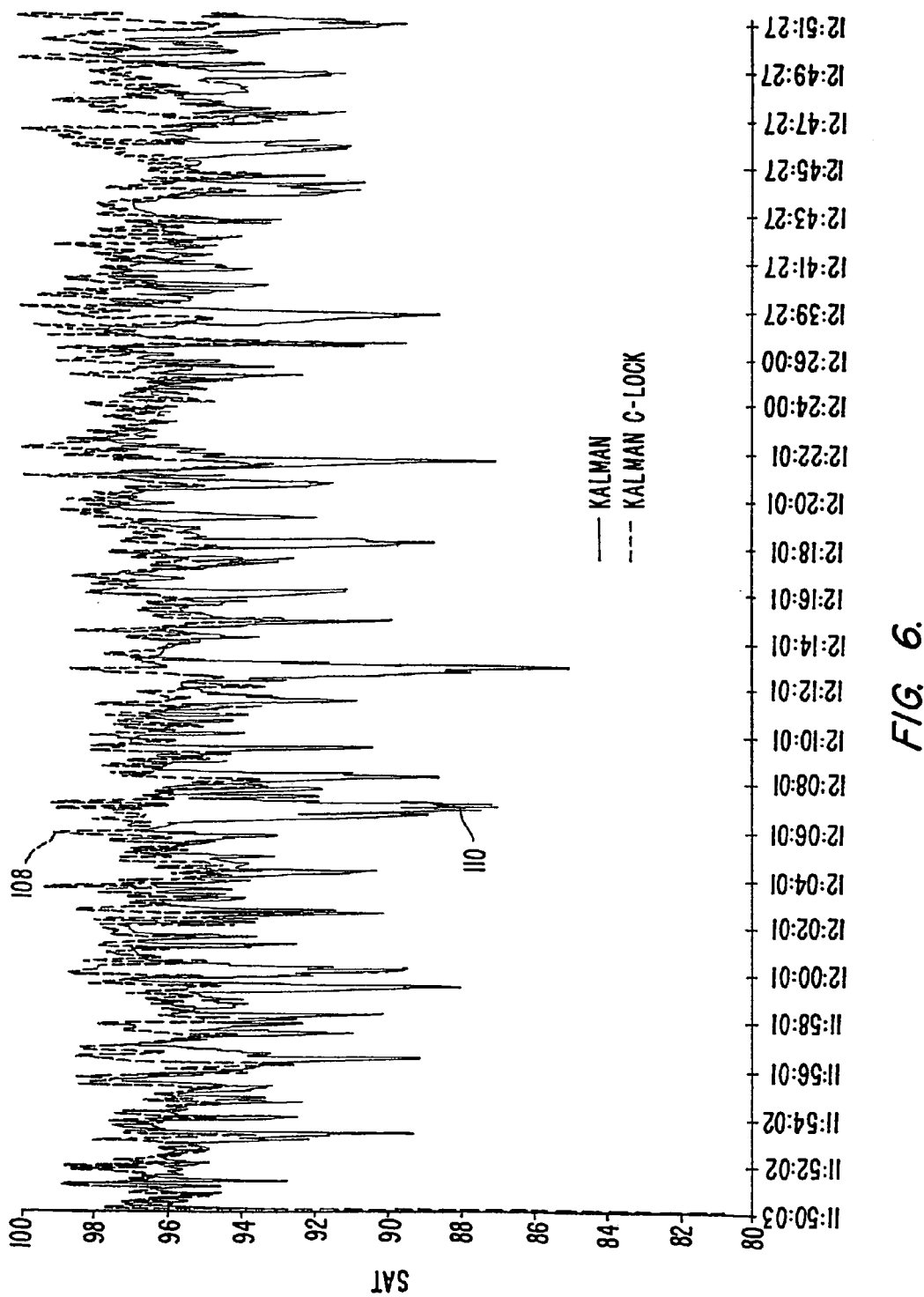
FIG. 6 is a graph illustrating the improvement in saturation calculation gained by enhancing the pulse shape with the Kalman cardiac gated averaging filter.

The Kalman cardiac gated averaging model automatically averages more data points if the incoming wave form varies quite a bit, yet has the ability to update quickly if the wave form obeys assumptions based on expected physiological variation. The Kalman cardiac gated averaging represents a significant improvement over prior art methods of calculating saturation as used in Nellcor oximeter models N200 and N3000, and as described in U.S. Pat. No. 4,802,486; U.S. Pat. No. 4,869,254; U.S. Pat. No. 4,911,167; U.S. Pat. No. 4,928,692; U.S. Pat. No. 4,934,372; U.S. Pat. No. 5,078,136; and U.S. Pat. No. 5,351,685 all assigned to Nellcor, the disclosures of which are all incorporated herein by reference. FIG. 5 shows an example of the inputs and outputs of a Kalman filter according to one embodiment of the invention. The trigger waveform 100 is from the R-wave of an ECG or from pulse rate calculation method 52 (FIG. 1). The raw data waveform 102 is at times quite corrupted by motion, yet by variable averaging, the Kalman cardiac gated averaging technique is able to keep the filtered waveform 104 looking quite regular. The estimated residual 106 correlates quite well in time with the noise on the measured data. FIG. 6 shows actual data processed by the series combination of the Kalman cardiac gated averaging and Kalman saturation algorithm (waveform 108) as compared to data processed with only the Kalman saturation algorithm (waveform 110). It is believed that there was no true desaturation (i.e., saturation below 90%) over the time period depicted, a fact reflected more accurately by the series combination of Kalman cardiac gated averaging and Kalman saturation averaging.

Figure 7:
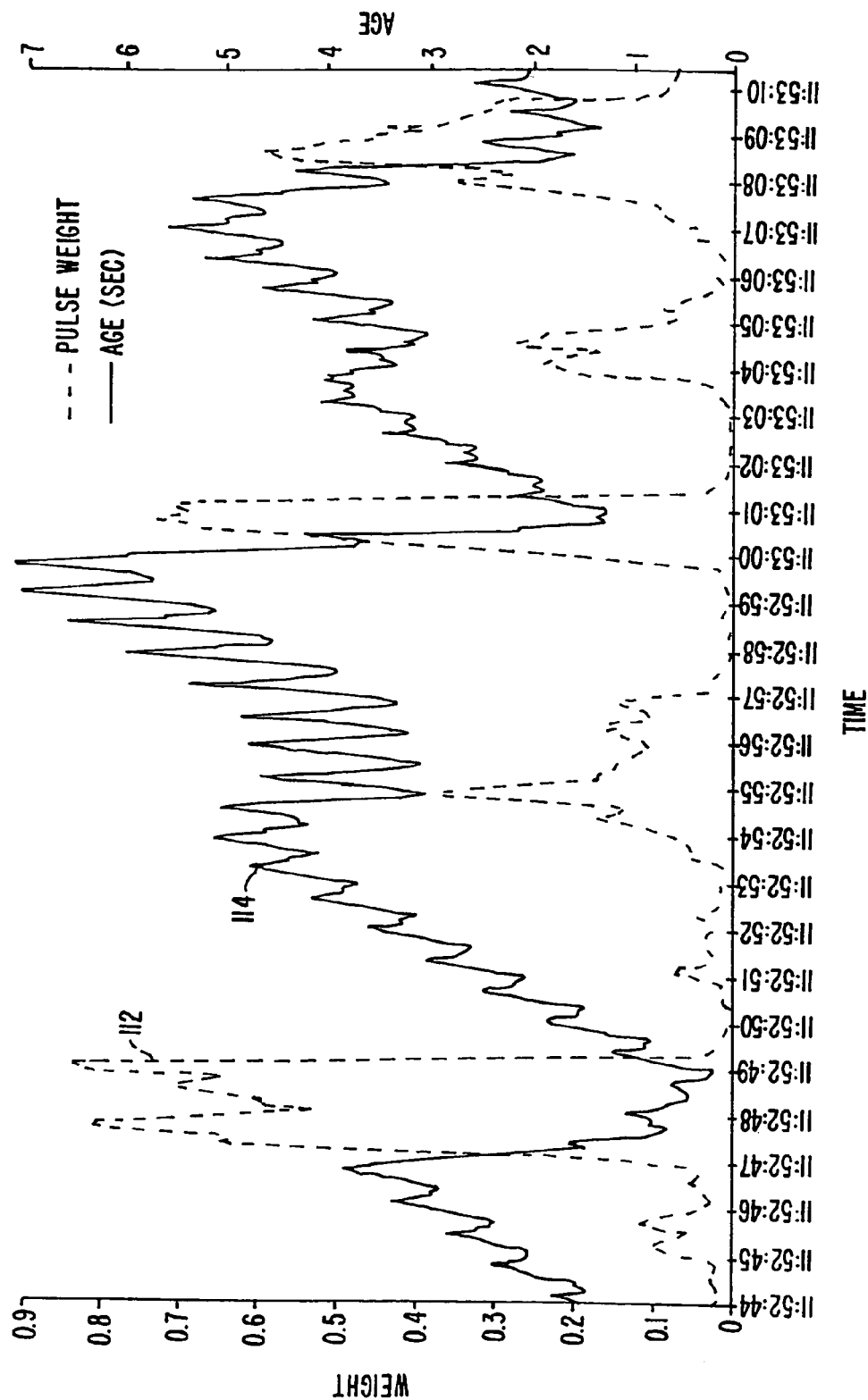
FIG. 7 is a graph illustrating the weighting and aging of pulses by one embodiment of a Kalman cardiac gated averaging filter.

FIG. 7 illustrates the relationship between the weight applied to the raw optical waveform, and the age of the filtered waveform according one embodiment of the Kalman cardiac gated averaging filter. The vertical axis on the left hand side of the graph represents the weighting and is associated with waveform 112. The right hand side vertical axis represents the age of the filtered waveform and is associated with waveform 114. It is important to note that as the weight applied to the incoming data decreases, the data employed in calculating the pulse rate ages correlatively.

Figure 8:
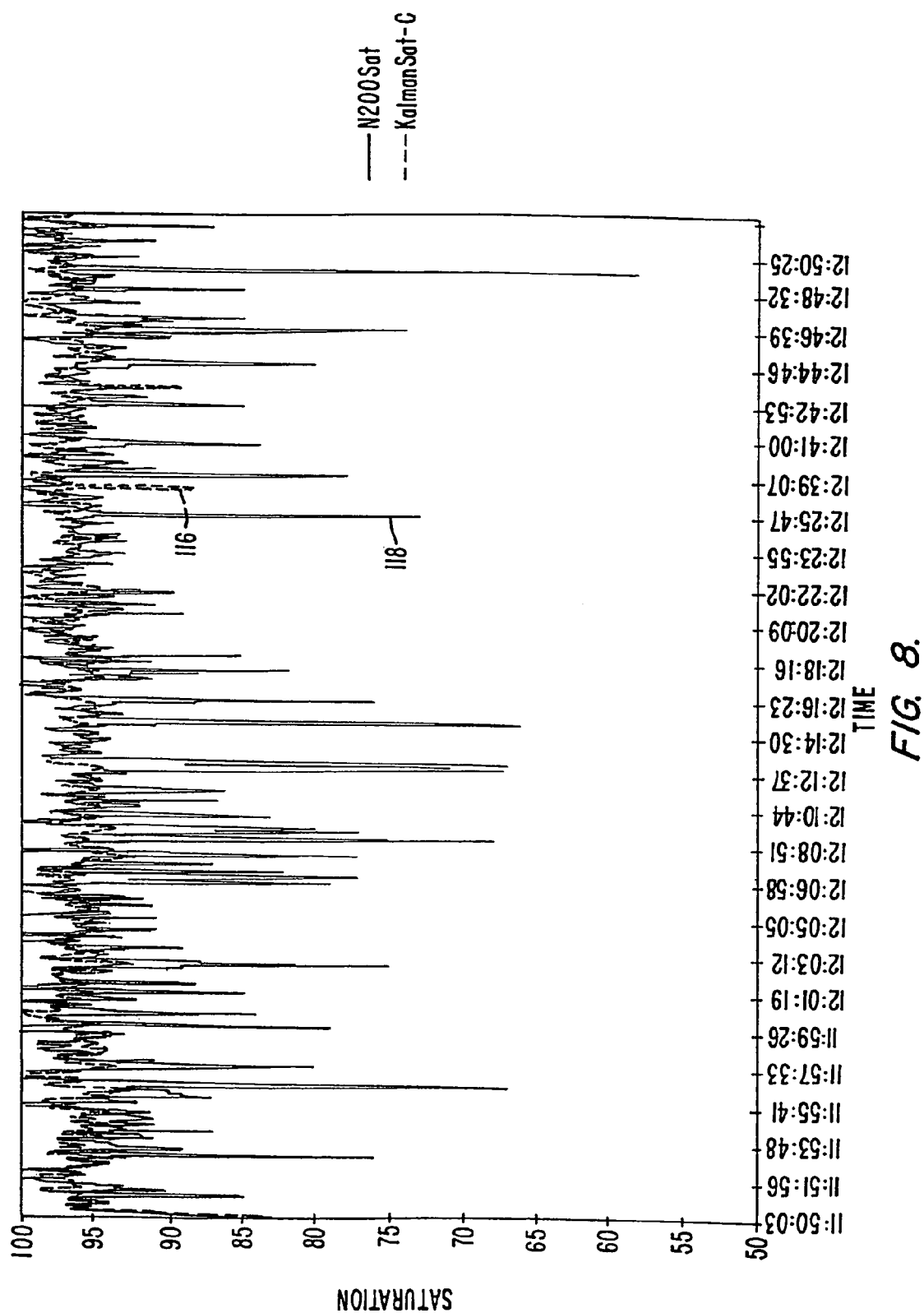
FIG. 8 is a graph illustrating the improvement in saturation calculation gained by employing both the Kalman cardiac gated averaging filter and the Kalman saturation algorithm.

FIG. 8 is a graph illustrating the improvement in saturation calculation gained by employing both the Kalman cardiac gated averaging filter and the Kalman saturation algorithm (waveform 116) as compared to the Nellcor N200 pulse oximetry system mentioned above (waveform 118). During this clinical trial, no true desaturation (i.e., saturation below 90%) is believed to have occurred.

Pulse Rate Calculation

In a preferred embodiment, a technique is employed to generate a robust pulse rate from the optical data for use as the Kalman cardiac gated averaging triggers instead of the ECG waveform which is typically obtained from impedance measurements. One prior art technique for determining a pulse rate from the optical pleth waveform is to count zero crossings. If there is no motion and no other noise, the optical pleth signal is very clean and a pulse rate can be determined by accurately counting zero crossings. During motion a zero-crossing approach will count transients from the motion and display an artificially high rate. Another prior art approach uses a template of the pleth signal corresponding to a single pulse and counts the number of matches with this template. However, during motion the signal may look nothing like the template and as a consequence, no pulse counting occurs.

The pulse rate calculator employed by the present invention estimates the frequencies and amplitudes of sinusoids in noise. Nehorai developed a procedure to find the frequencies and then the amplitudes and phases of a given number of arbitrary sinusoids in noise; Nehorai, A., *A Minimal Parameter Adaptive Notch Filter with Constrained Poles and Zeros*, volume 33 of the IEEE Transactions on Acoustics, Speech, and Signal Processing (1985), the disclosure of which is incorporated herein by reference. Nehorai and Porat extended this approach to specifically look for the fundamental frequency and then the amplitudes and phases of a harmonic signal in noise; Nehorai, A. and Porat, B., *Adaptive Comb Filtering for Harmonic Signal Enhancement*, volume 34 of the IEEE Transactions on Acoustics, Speech, and Signal Processing (1986), the disclosure of which is incorporated herein by reference. Hendry recognized a numerically more efficient procedure in finding the fundamental frequency based on Nehorai and Porat's approach; Hendry, S. D., *Computation of Harmonic Comb Filter Weights*, volume 41 of the IEEE Transactions on Acoustics, Speech, and Signal Processing (1993), the disclosure of which is incorporated herein by reference.

The technique employed by the present invention is referred to herein as Adaptive Comb Filtering (ACF). The pulse rate is calculated from the optical absorbance signal.

When viewed as a spectrogram (frequency versus time), the energy in a typical human pleth signal is distributed in a few stable, clearly defined bands corresponding to the harmonics of the pulse rate. The ACF first finds the fundamental frequency by defining a comb filter to notch out the energy of the signal, leaving only noise. The number of notches or signal harmonics in the signal is a matter of choice. For normal heart rates, four harmonics are preferred according to one embodiment, but other numbers may be preferred depending on the application, processor, computation power, and the low pass cutoff frequency of the bandpass filter 14. The ACF finds the harmonic frequency that defines the comb filter to cause the output noise outside the fundamental and chosen harmonics to have the smallest energy. The ACF searches for the fundamental by working out the first and second derivatives of the squared noise with respect to the fundamental to perform a Newton-Raphson search (described below), which is the classic approach to nonlinear minimization.

To formalize the minimization description, let y be the measured signal, x the harmonic signal, and n the noise $$y(t) = x(t) + n(t)$$

$$= \sum_{k=1}^{N} C_k \sin(k\omega t + \phi_k) + n(t)$$

In the z-transform domain, the comb filter is $$H(z^{-1}) = \frac{\prod_{k=1}^{N}(1 + \alpha_k z^{-1} + z^{-2})}{\prod_{k=1}^{N}(1 + \rho\alpha_k z^{-1} + \rho^2 z^{-2})}$$

where $$\alpha_k = -2 \cos k\omega_0$$

Figure 9:
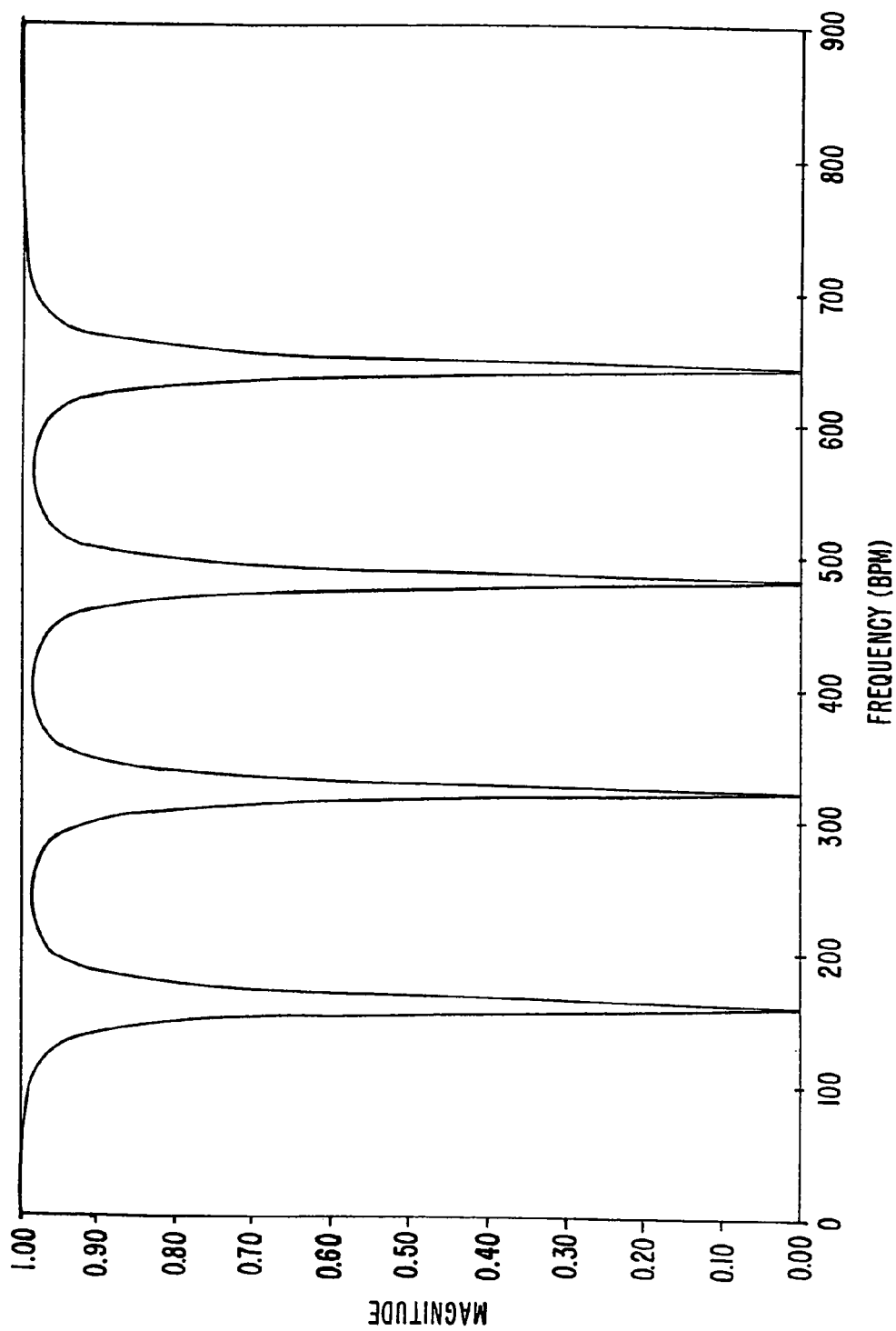
FIG. 9 is a frequency domain graph depicting the response of a comb filter.

The parameter $\omega_0$ is the fundamental frequency normalized by the sample rate. Each quadratic in the numerator of H introduces a zero on the unit circle at $\pm k\omega_0$. With $\rho<1$, the denominator introduces a pole inside the unit circle at $\pm k\omega_0$. The bandwidth of the notches is $\pi(1-\rho)$. FIG. 9 shows the frequency response of such a filter. The troughs correspond to a pulse rate of 150 beats per minute (BPM).

A brief summary of the derivation of the ACF follows. The error signal is the energy between the notches in the comb $\epsilon(t)=H(z^{-1})y(t)$. If the fundamental frequency is constant, and the error signal is measured for many time samples, a squared error may be defined $$V = \sum_j \varepsilon^2(t_j) = \varepsilon^T \varepsilon$$

Now the problem is to find the fundamental frequency that minimizes V. This is a nonlinear problem, thus requiring a Newton-Raphson search. First differentiate the squared error with respect to the fundamental frequency $$\frac{dV}{d\omega_0} + \varepsilon^T \frac{d\varepsilon}{d\omega_0} = -\varepsilon^T \psi$$

Nehorai and Porat show how to evaluate this first derivative. This term is set equal to zero to solve for the fundamental frequency, except that a nonlinear relationship still exists. Therefore, a Taylor series expansion must be taken about the current estimate of the fundamental frequency up to the linear terms $$\frac{dV}{d\omega_0} \approx \frac{dV}{d\omega_0(t-1)} + \frac{d^2V}{d\omega_0^2(t-1)}\Delta\omega_0(t) = 0$$

The second derivative of V is $$\frac{d^2V}{d\omega_0^2} = \psi^T\psi + \varepsilon^T\frac{d^2\varepsilon}{d\omega_0^2}$$

$$= \psi^T\psi - \varepsilon^T\frac{d\psi}{d\omega_0}$$

$$\cong \psi^T\psi$$

In the Newton Raphson method, the second derivative of the error is typically set to zero because it is often small and complicated to calculate. Then solve for the update to the estimated fundamental frequency $$\omega(t) = \omega(t-1) + \Delta\omega(t-1)$$

$$\Delta\omega(t-1) = \frac{\varepsilon^T\psi}{\psi^T\psi}$$

In practice it is desirable to estimate the fundamental frequency as the data comes in, and allow the frequency to change slowly in time. This approach of using the instantaneous values of the error and its derivatives is called the least mean square (LMS) approach. In the LMS approach, the instantaneous values must be smoothed, otherwise using the update $$\Delta\omega_0(t-1) = \frac{\varepsilon\psi}{\psi^2}$$

results in erratic behavior in the fundamental frequency update. Nehorai and Porat proposed using $$\Delta\omega_0(t-1) = \frac{\gamma(t)\varepsilon\psi}{r(t)}$$

$$r(t+l) = (l-\gamma(t+l))r(t)+\gamma(t+l)\psi^2(t+l)$$

where $\gamma(t)$ is a time varying constant that is always less than one, keeping the update small, and $r(t)$ is a low-pass filtered version of $\psi^2(t)$.

The derivative of the measurement error is then evaluated with respect to the fundamental frequency. First, it must be noted that the numerator in H can be rewritten as $$A(z^{-1}) = \prod_{k=1}^{N}(1+\alpha_k z^{-1}+z^{-2})$$
$$= 1+a_1 z^{-1}+\cdots a_n z^{-n}+\cdots a_1 z^{-2n+1}+z^{-2n}$$

Then the derivative can be evaluated using the chain rule $$\psi(t) = -\frac{d\varepsilon(t)}{dt}$$
$$= -\sum_{i=1}^{n}\frac{\partial\varepsilon}{\partial a_i}\frac{\partial a_i}{\partial\omega_0}$$

The steps of the ACF algorithm according to the present invention follow. First, the $a_i$'s in the vector a are defined. It turns out that given $$b_i = -b_{i-1}\frac{\sin((n+1-i)\omega_0/2)}{\sin(i\omega_0/2)}$$

then $$a_i = a_{i-1}+b_i$$

with $a_0=b_0=1$. A distinction may also be made between the current error given the last estimate of the fundamental frequency, called the prediction error $\epsilon(t)$, and the current error given the current estimate of the fundamental frequency, called the a posteriori prediction error $\bar{\epsilon}(t)$. The difference is subtle, but Nehorai found the convergence rate improved with this distinction.

The ACF algorithm begins with initializing all errors to zero and initializing the filter coefficients with the best guess of the fundamental frequency. In one embodiment, a fixed value of $\rho=0.98$ is used and the following ACF algorithm is iterated 1. Make a measurement and evaluate the prediction error $$\varepsilon(t) = y(t)+\sum_{i=1}^{2n}y(t-i)a_i-\sum_{i=1}^{2n}\bar{\varepsilon}(t-i)\rho^i a_i$$

The input measurement in this preferred implementation is the derivative of the normalized IR data (e.g., from box 18 of FIG. 1a). Using the derivative emphasizes the higher frequencies so that the noise energy is more evenly distributed, or "whitened", which improves the tracking performance of the adaptive comb filter.

2. Update the fundamental frequency $$\omega_0(t) = \omega_0(t-1)+\frac{\gamma(t)}{r(t)}\psi(t)\varepsilon(t)$$

3. Update the filter coefficients $$a_i = a_{i-1}+b_i$$

4. Using the notation $\nabla i = \delta a_i/\delta\omega_0$, update the derivatives of a with the following recursive formula $$c_0 = 0$$

$$\nabla_i = \nabla_{i-1}+c_i b_i$$

$$c_i = c_{i-1}+\frac{(k+1-i)\cos((k+1-i)\omega_0/2)}{2\sin((k+1-i)\omega_0/2)} - \frac{i\cos(i\omega_0/2)}{2\sin(i\omega_0/2)}$$

5. Update the a posteriori prediction error $$\bar{\varepsilon}(t) = y(t)+\sum_{i=1}^{2n}y(t-i)a_i-\sum_{i=1}^{2n}\bar{\varepsilon}(t-i)\rho^i a_i$$

6. Calculate a filtered version of $\bar{\epsilon}$ $$\bar{\varepsilon}_F = \frac{\bar{\varepsilon}}{A(\rho z^{-1})}$$

$$\bar{\varepsilon}_F(t) = \bar{\varepsilon}(t)-\sum_{i=1}^{2n}\bar{\varepsilon}_F(t-i)\rho^i a_i$$

7. Calculate a filtered version of y $$y_F(t) = \frac{y(t)}{A(\rho z^{-1})}$$

$$y_F(t) = y(t)-\sum_{i=1}^{2n}y_F(t-i)\rho^i a_i$$

8. Update $\delta\epsilon/\delta\omega_0$ $$\psi(t+1) = \sum_{i=1}^{2n} y_F(t-i)\nabla_i - \sum_{i=1}^{2n} \overline{\epsilon_F}(t-i)\rho^i \nabla_i$$

9. Update the constants used to keep the LMS approach stable. In one embodiment, $\lambda_0=0.98$.

$\lambda(t+1)=\lambda_0\lambda(t)+(1-\lambda_0)$ $\gamma(t+1)=\gamma(t)/[\gamma(t)+\lambda(t+1)]$ $r(t+1)=r(t)+\gamma(t+1)[\psi^2(t+1)-r(t)]$ 10. Estimate the bandpass gain of H as the gain at DC.

$K(t)=A(1, t)/A(\rho, t)$

11. Estimate the harmonic signal as the difference between the measured signal and the prediction error corrected for non-unity bandpass gain.

$x(t)=y(t)-\epsilon(t)/K(t)$

12. Repeat the process as long as data keeps coming.

When a reliable estimate of the fundamental frequency has been determined, it is preferred to at least occasionally calculate the harmonic amplitudes. A description of a technique for calculating the harmonic amplitudes follows.

As will be shown, it is useful to know the amplitudes of the harmonics. The power of each of the first n=4 harmonics is estimated by taking an RMS of the output of a comb filter having only one "tooth" tuned to the frequency of that harmonic. This allows the power of the harmonics to be estimated with a minimal number of computations. This process can be performed independently of the adaptive comb filter provided the heart rate estimate is made available to this process. For each harmonic k, the steps in the harmonic estimation are:

1. Calculate a for $k\omega_0$ $a_1=-2 \cos k\omega_0, a_0=a_2=1$

2. Calculate the output of the "single toothed" comb filter at $k\omega_0$ $$\epsilon(t) = y(t) + \sum_{i=1}^{2} y(t-i)a_i - \sum_{i=1}^{2} \overline{\epsilon}(t-i)\rho^i a_i$$

3. Estimate the bandpass gain of the "single toothed" comb filter at $k\omega_0$ as the gain at DC $$K(t) = \frac{\sum_{i=0}^{2} a_i}{\sum_{i=0}^{2} \rho^i a_i}$$

4. Estimate the harmonic signal at $k\omega_0$ as the difference between the measured signal and the output of the "single toothed" comb filter.

$x(t)=y(t)-\epsilon(t)/K(t)$

5. Estimate the power (pwr) in the harmonic at $k\omega_0$ using a cascaded IIR filter $pwr(t)=\lambda pwr(t-1)+(1-\lambda)x(t)^2$ $pwr'(t)=\lambda pwr'(t-1)+(1-\lambda)pwr(t)^2$ where $\lambda=0.99$ As described above, an improvement is achieved in both the saturation calculation and cardiac gated averaging algorithms with the use of a Kalman model to optimally filter updates. Therefore, in a particular embodiment, the final pulse rate displayed is also the output of a Kalman filter where the input is the change in rate from the above approaches. The Kalman model is $\Delta\omega'=0+n^Q$ $\Delta\omega=\Delta\omega'+n^R$ Where $n^Q$ is the physiologically possible change in rate, $n^R$ is the measurement noise, $\Delta\omega_0$ is the update from the ACF, and $\Delta\omega_0'$ is the Kalman estimate of the update. The standard deviation of $n^Q$ was modeled to be 5 BPM.

According to a preferred embodiment, implementation precision requirements are achieved as follows. Given coefficients $a_k=-2 \cos k\omega_0$ the gain of the numerator of the comb filter, $$A(z^{-1}) = \prod_{k=1}^{N} (1 + a_k z^{-1} + z^{-2})$$

for small $\omega_0$, z=1, and N=4, converges to $$A(z^{-1}) = \prod_{k=1}^{N} (k\omega_0)^2 = \omega_0^{2N} \prod_{k=1}^{N} k^2 = 576\omega_0^8$$

At 30 BPM, $\omega_0$ is approximately 0.055 and the gain of the numerator is approximately 4.8e-8, with coefficients of a having magnitudes ranging from roughly 1 to 100. Thus a small error in the calculation of one of the coefficients of a can produce a huge error in the gain of the numerator of the filter. It has been observed that about 32 bits of floating point precision are required to calculate a so that the gain is reasonably preserved at 30 BPM. Note, however, that if the $\omega_0$ is doubled, the gain increases by 256-fold, reducing the precision requirement by 8 bits. The precision requirements for the denominator of the comb filter are similar. The effect of not having enough precision is that the comb filter become unstable at these low rates.

For one preferred embodiment using an analog-to-digital sampling frequency of approximately 5 MHz, it is preferred to subsample the input by a factor of 2, which effectively doubles $\omega_0$. Using $\rho=0.96$ with subsampling by a factor of 2 produces a comb filter of equivalent performance to that described above with $\rho=0.98$ and no subsampling. Furthermore, the gain itself can be calculated with greater precision in floating point because it is calculated as a series of multiplications rather than additions. The actual gain of the numerator, or denominator, can also be calculated by adding the coefficients of a. It is preferred to compare the actual and expected gains and adjust the middle coefficient of a by the difference. These two optimizations permit the adaptive comb filter to track rates down to 30 BPM using single precision floating point arithmetic without becoming unstable.

Pattern Matching Rate Calculator

There are times when the ACF by itself is not sufficient to track a patient's heart rate This is the case with arrhythmias, where the energy is not concentrated in a few trackable harmonics. Also, a patient's heart rate can change more rapidly than the ACF is capable of tracking, or change dramatically during a period of motion in which the ACF failed to correctly track the change. An alternative pleth rate calculator is therefore included in the present invention that does not require a harmonic signal, and is not based on an adaptive algorithm. This alternative rate calculator is not as robust during motion as the rate calculator described above, but is intended to be used when the ACF cannot track the rate.

A feature that is common to all human pulses is that they go up and down and have some minimum period corresponding to about 250 BPM, i.e., 240 msec. Given this model of a human pulse, there is a crest during each pulse such that the current value of the pulse waveform is the maximum value that has been seen for the past 240 msec followed by a trough during that same pulse where the current value is the minimum value that has been seen for the past 240 msec. The pattern matcher of the present invention identifies sequences of crests and troughs that preferably do not trigger any motion detection criterion (discussed below), and computes the rate from the average period of all such patterns which have been identified in the past 512 signal samples. According to a preferred embodiment, the optical signal is nominally sampled 57 times each second, 512 samples therefore corresponding to roughly 9 seconds. In one embodiment, the pattern matcher uses a minimum period of 210 msec instead of 240 msec to make allowances for limited motion artifact and an oximeter sampling rate in excess of 57 Hz. The pattern matching rate is updated each time such a pattern is identified. In some preferred embodiments, motion detection criterion based on the shape of the pulse have been adapted to reject pulses which are potentially contaminated by motion artifact.

According to a preferred embodiment, the motion detection criterion require the calculation of the maxima, minima, and average for the current and previous detected patterns. Motion is detected when any of the following criterion are met:

a) the maximum of the current pattern is significantly farther away from the average of the current pattern than the minimum is (e.g., the ratio of differences is greater than 1.02);
b) criterion a) failed on the last detected pattern;
c) the maximum of the current pattern is significantly farther away from the average of the current pattern than the average of the current pattern is from the average of the current and previous minima; or
d) the difference between the average of the current and previous patterns is greater than half the difference between the current maximum and minimum (big DC shift).

A motion flag is set whenever any of the motion detection criterion are met and is cleared whenever none are met for two consecutive patterns.

In a preferred embodiment, two pattern matching rate calculators are run in parallel. One receives the bandpassed normalized waveform as input. The second receives a filtered form of the first derivative of the pleth. The use of two inputs with different characteristics minimizes the time that motion is incorrectly reported. Each pattern matcher stores the proportion of patterns for which its motion metrics indicate motion. The pattern matcher that reports the least motion over the last ten seconds is used for the pattern matching rate. This dual pattern matcher reports that motion is present only when the motion metrics for each of its two pattern matchers indicates motion.

Exception Handling for Rate Calculator

As discussed above, the adaptive comb filter (ACF) employed by the present invention tracks a signal having N harmonics. It sometimes happens that motion artifact causes the ACF to track the wrong rate, and when the motion stops, the "teeth" on the comb may be on a harmonic rather than the fundamental. For example, the fundamental of the ACF could be tracking the second harmonic of the pleth, or the 2nd harmonic for the ACF could be tracking the fundamental of the pleth. These situations would cause the ACF to report twice or half the correct pulse rate, respectively. This could happen if the ACF was initialized to the wrong rate and settled on a harmonic or subharmonic, or if the rate changed more suddenly than the ACF could track. In general, the ACF is quite stable, and several minutes of prolonged, vigorous motion may be required before it locks onto a harmonic or subharmonic of the pulse rate. However, because of the potential for false reporting, according to a preferred embodiment a number of rules are used to calculate a more accurate rate.

A simple model of most plethysmographs, i.e., pleths, may be compared to a sawtooth-like pattern for which the amplitude of the harmonics of the pleth fall off by a factor of 2 for each harmonic. Thus, for most pleths, the falloff is fairly rapid. However, some patients have nearly half the energy of their pulses contained in the second harmonic. Other physiological pleth patterns may contain significant amounts of energy at multiples of one-half the pulse rate, while still others may have strong respiratory components at one-half the pulse rate, although the signal at the pulse rate should still be dominant. Arrhythmias may have no repeating pattern, thus violating the model assumed by the ACF. When the ACF locks onto a subharmonic, or some superharmonic, the "tooth" on the comb that passes the greatest amount of energy will not correspond to the fundamental frequency estimated by the ACF. Table 1 shows relative harmonic amplitudes for a typical pleth.

TABLE 1

| 1st Harmonic | 2nd Harmonic | 3rd Harmonic | 4th Harmonic |
|---|---|---|---|
| 82.8% | 14.4% | 2.1% | 0.5% |

For most patients, where there is little or no motion, all the energy in the pleth is at the fundamental or a harmonic of the pulse rate. Although pulse rates will vary cyclically in response to various mechanisms, plateaus in the pulse rate will be long enough, and frequent enough, that the autocorrelation has a very high value at the fundamental of the pulse rate at these times. Where there is significant energy at a subharmonic of the pulse rate, the autocorrelation at the subharmonic may be higher than at the pulse rate, but the autocorrelation function will still have a strong local maxima at the pulse rate.

For an arrhythmia with a non-repeating pattern, the autocorrelation may not have any strong local maxima. However, if a patient is not moving, the pleth will be modulated only by the patient's pulse, and will thus be completely correlated in the IR and red channels. Motion artifact, however, causes the IR and red channels to become less correlated. This crosscorrelation can thus be used as a rough indicator of the degree of motion and therefore the reliability of the rate reported by the pattern matching.

In view of the foregoing, a concise set of rules is desirable that reliably enables the ACF to resume tracking the correct pulse rate when motion has stopped, and which does not increase the chance that ACF will track the wrong pulse rate. An "uncorrelation" metric is calculated which is defined as:

$$\sqrt{1-\text{crosscorrelation}(IR, red)^2},$$

where the crosscorrelation is currently calculated over 512 points of the normalized data.

The magnitude of each of the N=4 harmonics is estimated each second, and the magnitude information is used to calculate a measure of the validity of the pulse. In addition to estimating the pulse rate, the ACF also calculates filtered signal and noise waveforms, X and $\epsilon$ using the comb filter, which enables the calculation of a signal to noise (S/N) ratio. The S/N ratio is expected to be high for non-arrhythmic patients who are not moving, and low during motion or arrhythmias. It is also low if the fundamental of the heart rate does not match any of the harmonics being tracked by the ACF. In various embodiments, the S/N may be calculated using both whitened and unwhitened pleths with the best S/N ratio being used.

The validity measure is calculated as follows:
1) Calculate the magnitude of each of the harmonics of the pleth. Correct the magnitudes for any bandpass filtering that occurred earlier in the processing chain. Normalize the harmonics so that they add up to one, and IIR filter with a time constant of 0.1/second.
2) Take the logarithm of the filtered energy estimate for each harmonic. For each harmonic excluding the fundamental, take the difference between the logarithm for that harmonic and the logarithm for the previous harmonic. Bound the difference by ±1.5. Calculate the average of all of these N−1 differences to estimate the exponential decay rate for the harmonics of the pleth, and IIR filter this average with a time constant of 0.3/second.
3) While calculating the unfiltered exponential decay rate, also calculate the standard deviation between the exponential decays of the pairs of harmonics and the previous filtered exponential decay rate. IIR filter this standard deviation with the same time constant used for the filtered exponential decay (0.3/second).
4) Subtract the filtered standard deviation from the filtered exponential decay to get the validity measure.

Figure 10:
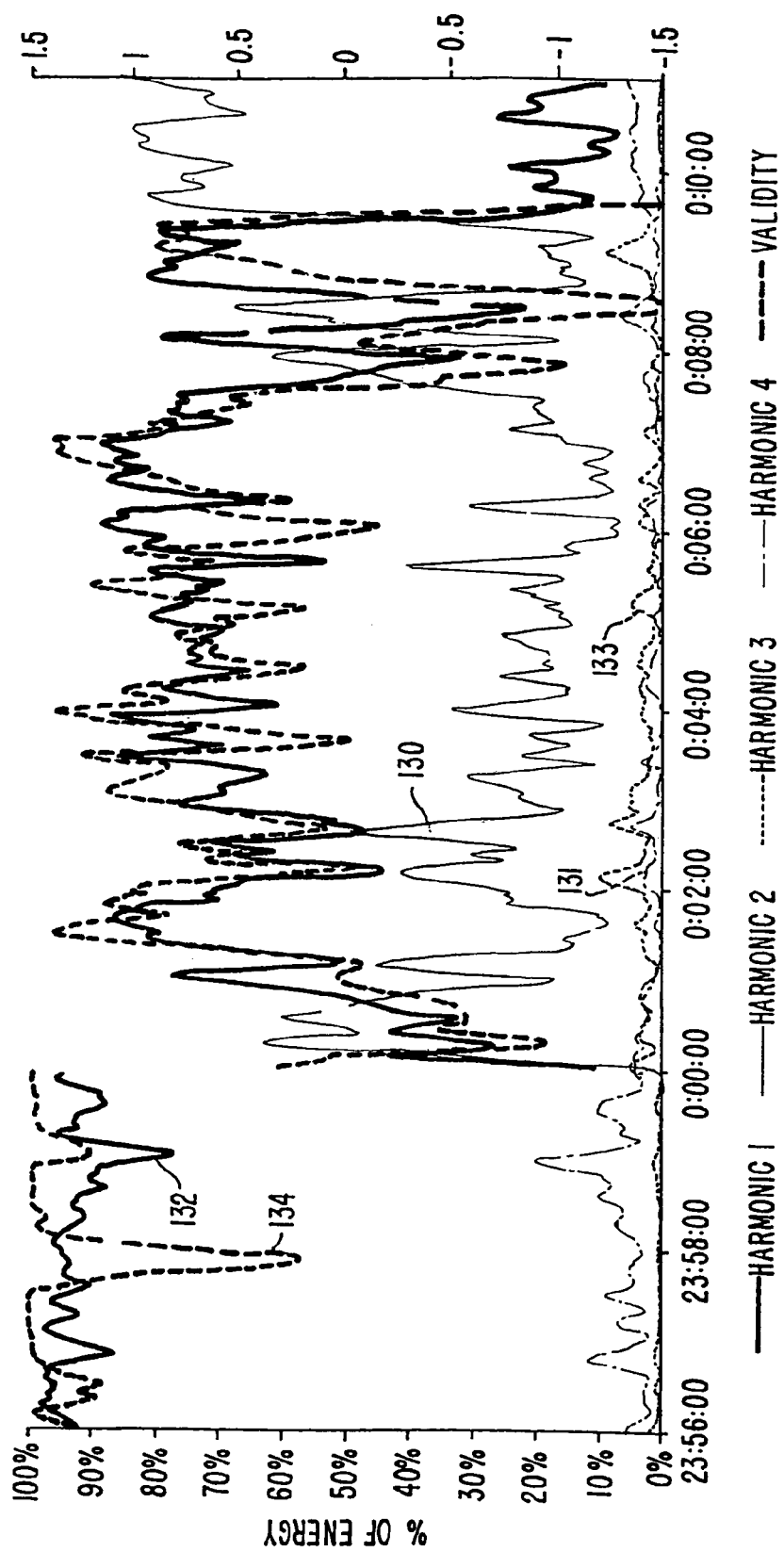
FIG. 10 is a graph showing the validity measure for data pulses in relation to the relative strengths of several signal harmonics.

The best pleth, according to this validity measure, will have the energy in consecutive harmonics falling off exponentially with a decay rate of at least $e^{1.5}$ (about 4.5-fold). If a majority of the energy in the pleth is calculated to be in one of the harmonics instead of the fundamental, the standard deviation for the exponential decay will probably be large enough to drive the validity measure negative. The validity measurement preferably should have a response time of about 12–13 seconds. FIG. 10 shows the validity measure 134 and relative strength of the four harmonics (130–133) of the pleth signal. When the strength of the higher harmonics, e.g., waveform 130, goes above lower harmonics, e.g., waveform 132, the validity index 134 goes appropriately down.

The following mechanisms may be used to assure that the ACF is tracking the right rate. Every 10 seconds a Fast Fourier Transform (FFT) (power spectrum) may be performed on the IR pleth and each peak in the spectrum may be evaluated prospectively to find the rate which would give the highest confidence measure for the ACF (the formulas used to combine various metrics into a confidence measure for the ACF rate are described in a subsequent section of this application). This is possible because the magnitude of each of the harmonics that would be tracked by the ACF at a given rate can be estimated by adding up the energy in several adjacent frequencies of the FFT. According to one preferred embodiment, one can use a 512 point FFT and model a harmonic as 3 adjacent frequencies.

The ACF rate is reset to this rate if the following conditions are met:
a) The current ACF confidence measure is less than 50 OR the ACF has not been initialized by this mechanism yet.
b) The prospectively estimated confidence measure for the new rate is at least 50.
c) The prospectively estimated S/N for the new rate is at least 0.7.
d) The new rate is within 10 BPM of a local maxima on the autocorrelation curve, and that local maxima is positive.
e) The best rate estimated by this method is within 15% of the best rate estimated by this method 10 seconds ago.

Note that no ACF rate is ever reported until it has been initialized by this mechanism.

Figure 11:
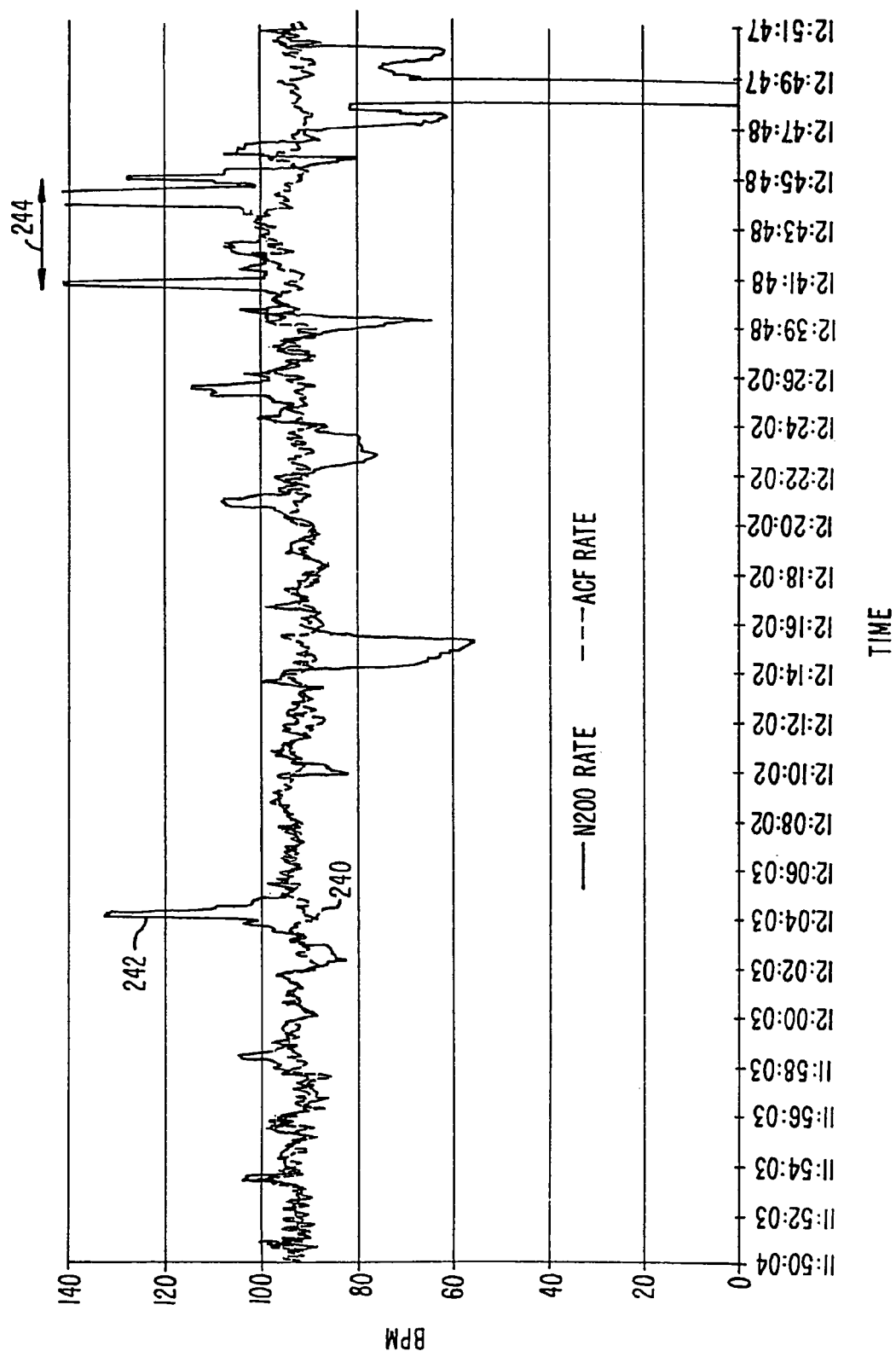
FIG. 11 is a graph showing the pulse rate reported by the adaptive comb filter employed by the present invention as compared to the pulse rate reported by a prior art system.

FIG. 11 shows a comparison between the pulse rate 240 calculated by the ACF with the additional rules disclosed above as compared to the pulse rate 242 reported by a prior art system. During a period of motion (244), an inaccurately high pulse rate is reported by the Nellcor N200 oximeter. The ACF designed according to the present invention which applied these exception handling rules tracked the rate accurately through the motion.

Post-Processing and Display

In this section, preferred methods of processing and displaying the arterial oxygen saturation and pulse rate for use on a hospital floor are described. Given available metrics from the above-described algorithms, confidence levels for the saturation and the heart rate are estimated, thus determining which saturation and which heart rate of the multiple heart rates and multiple saturations (calculated in the systems of FIG. 1a and 1b) should be considered more reliable, and how long the saturation or heart rate previously selected should be held when a current estimate is not considered sufficiently reliable.

The present invention calculates the following values: the ACF heart rate, from the adaptive comb filter; the pattern matching heart rate; saturation using a Kalman filter without cardiac gated averaging; and saturation using a Kalman filter in combination with a Kalman-filter-based cardiac gated averaging technique. Several metrics are also calculated and can be used to predict the confidence of the saturations and heart rates. These include for the ACF heart rate:

| | |
|---|---|
| Validity: | a heuristic metric based on the strength of harmonics in the pulse, i.e., the shape of the pulse; |
| S/N: | signal-to-noise ratio; |
| Arrhythmia probability: | a function of S/N vs. Uncorrelation averaged over 20–100 seconds; and |
| Uncorrelation of IR and red: | $\sqrt{1-\text{crosscorrelation}(IR, red)^2}$ where crosscorrelation is over 512 sample points |

For the pattern matching heart rate:

| | |
|---|---|
| Motion flag: | set when motion is detected; and |
| Motion Percent: | percentage of motion corrupted patterns detected in the last ten seconds |

For saturation using only a Kalman filter:

| | |
|---|---|
| Age: | effective averaging period is double this; and |
| Variance: | standard deviation of saturation estimate in saturation points |

For saturation using a Kalman filter in combination with Kalman-filter-based cardiac gated averaging (CGA):

| | |
|---|---|
| Age: | effective averaging period is double this; and |
| Variance: | standard deviation of saturation estimate in saturation points |

Several metrics are calculated independent of saturation or heart rate. These include:

| | |
|---|---|
| % IR Modulation | |
| Contact status: | from contact electrodes of sensor (used in a preferred fetal sensor as described in commonly assigned U.S. Pat. No. 5,247,932, the entire disclosure of which is incorporated herein by reference); |
| Light level | |
| IR Spectrum: | 128 sample points; and |
| Uncorrelation of IR, red: | 128 sample points for faster response |

At 100% saturation the confidence intervals for the saturation values calculated using only a Kalman filter are:

>95% confidence if (0.13*Variance+0.053*Age)<1

>80% confidence if (0.10*Variance+0.036*Age)<1

>50% confidence if (0.08*Variance+0.015*Age)<1

When the 50, 80, and 95% confidence lines are plotted in Age-Variance space, the lines come very close to having a common origin, so that the confidence level can be estimated continuously as a function of the slope of a line from that origin. The 95–100% confidence interval covers a disproportionately large area in the Age-Variance space, so the confidence interval should be adjusted if it is over 95%. For lower saturations, the Variance is reduced as a function of the saturation by up to 60% at a saturation of 50. This reflects the fact that fixed variance in ratio-of-ratios will have an increasing effect on the saturation estimate as the saturation declines. The confidence intervals for saturation values calculated with the Kalman-filter-based cardiac gated averaging are the same as above except that Age is first divided by 2, because the cardiac gated averaging can result in an older but more accurate saturation value.

The confidence interval for the ACF heart rate is a function of the validity metric and the arrhythmia probability metric. This space divides into several regions in which one or both metrics are the determining factor in how likely the adaptive comb filter is to be tracking the correct rate.

For the pattern matching heart rate, the confidence interval is set to 100% less the Motion Percent metric.

According to a preferred embodiment, if one saturation has a confidence interval at least 10% higher than the other, it is the best saturation. If the two saturations have confidence intervals within 10% of each other, the best saturation will be calculated as a linear interpolation between the two saturations, with their variances and ages also being linearly interpolated for recalculation of the confidence interval of the best saturation. If the interpolated saturation has an age greater than 35 seconds, but either the non-CGA saturation or the CGA saturation has an age less than 35 seconds, the saturations will be re-interpolated so that the interpolated saturation has an age of 35 seconds. The interpolated saturation is then smoothed out with an adaptive filter that looks at the rate of saturation change and results in a slight increment to the age of the interpolated (best) saturation.

Similar criteria are used for interpolation of the heart rates, except that no check needs to be made of the age of the heart rates, as they are generally quite recent, i.e., less than 10 seconds old.

The Age and Variance metrics for the saturation algorithms are calculated according to one embodiment of the invention in the following manner. A general algorithm for calculating the age of the output of an IIR filter having the form $$\text{Filtered}(n+1)=(1+W)*\text{Filtered}(n)-W*\text{Raw},$$

where the age of Filtered and Raw are known, and Filtered (n) is the value at sample number n, is described by the following steps:

1) Increment the age of Filtered by the amount of time elapsed since it was last calculated; and
2) Age of Filtered(n+1)=(1+W) *Age of Filtered(n)+W *Age of Raw According to the present invention the term W is calculated as follows. In all instances, K represents the gain of the Kaman filter. In all instances, W is equal to the amount by which Filtered is incremented divided by the difference between Filtered and Raw. That is, with respect to the saturation algorithms of the present invention, $$W=\text{Satincrement}/(\text{InstantaneousSat}-\text{FilteredSat})$$

For data points calculated using Kalman-based CGA, $$\text{filtered}(n+1)=(1-K)*\text{filtered}(n)+K*\text{raw}$$

therefore, W=K.

For saturation using only a Kalman filter, $$\text{filteredsat}(n+1)=(1-K)*u*\text{filteredsat}(n)+K*v$$

where u and v are transforms of the raw IR and red values such that the instantaneous rawsat=v/u. Therefore, $$\text{filteredsat}(n+1)=(1-K)*u*\text{filteredsat}(n)+K*u*v/u$$

or $$\text{filteredsat}(n+1)=(1-K)*u*\text{filteredsat}(n)+K*u*\text{rawsat}$$

therefore, W=K*u.

If Kalman filtering of the derivative of saturation (d(sat)/dt) is included in the embodiment, filteredsat($n+1$)=(1−$K$)*filteredsat($n$)+$K$*rawsat therefore, W=K.

The calculation of saturation Age is accomplished according to the following chain of events. Initially, the value Age is the delay of the bandpass filter, if one is included in the embodiment. Age is then passed to the Kalman CGA (if included in the embodiment), which stores the age of each filtered point on the pulse, updates the age of the appropriate point, and sets Age to that of the IR and red values output. Age is then passed to the Normalization routine (if included in the embodiment), which buffers and sets Age to the value from half a window ago, plus half the window length. Age is then passed to the saturation algorithm (assume Kalman saturation algorithm), which sets Age to the age of the saturation estimate. Finally, Age is passed to the Kalman dSat/dt calculator (if included in the embodiment this provides some incremental smoothing of saturation as well as calculates dSat/dt), which sets Age to the age of the final sat estimate.

The calculation of the Variance metric for the saturation algorithms is as follows. When the saturation is not changing, the following is true:

filteredsat=$v/u$, or filteredsat=rawsat

When saturation is changing, the difference between estimated and actual saturation is:

satdifference=$v/u$−filteredsat

The Kalman saturation calculation includes a residual term, R, which is equal to the mean square over some window of:

$v-u$*filteredsat, or $u$*(rawsat−filteredsat), or $u$*satdifference and also includes the term usizebar which is equal to the mean square of u over that window. Therefore, satvariance=$R$/usizebar Since the Kalman saturation algorithm is an IIR filter, the inputs that contribute to its current saturation estimate cover a longer period of time than that which is covered by the finite window used to calculate R and usizebar. The variance for all of these inputs that are contributing to the saturation estimate is calculated in the same manner as the age of the saturation estimate, that is, satvariance($n+1$)=(1−$W$)*satvariance($n$)+ $W$*$R$/usizebar The standard deviation in saturation points is given by satStDev=100*$\sqrt{\text{satvariance}}$ According to a preferred embodiment, independent of the confidence metrics for saturation and heart rate, several properties of the incoming oximetry signal are evaluated in order to determine if the signal is actually due to a human pulse and what action the display should take. The possible states include:

| | |
|---|---|
| Disconnect: | when the sensor is unplugged; |
| No Contact: | when the sensor is a fetal sensor and the contact electrodes do not indicate contact with the patient; |
| Pulse lost | when the pulse disappears and the sensor is still on the patient; |
| Non-pulse | when the oximetry signal comes from a signal other than a human pulse because the sensor has fallen off or is seeing an enormous amount of interference; |
| Pulse Present | when the oximetry signal comes from a human pulse; and |
| Not Sure | a waiting period before declaring a Disconnect or Non-pulse state. |

The possible actions in response to the occurrence of these various states are to update the display, hold the current values, or clear the display, e.g., blanks, dashes, zeroes, etc. Some additional values are calculated for use in evaluating the states and the possible actions. The maximum and minimum light levels over the past 15 seconds are calculated (½ second sampling) by comparing amplitudes of the signal sample points after they are bandpass filtered by filter 14, but prior to being normalized. In addition, a value called Allen's threshold is calculated which is a percentage modulation threshold indicative of a sudden loss of pulse. This value is set to zero when the ratio of the maximum and minimum light levels over the past 5 seconds is greater than 1.5. Otherwise it is set to ⅙ of the IR percent modulation if that value is greater than the current Allen's threshold. Otherwise, Allen's threshold decays with a 5 second response time if the current percent IR modulation is non-zero and is either less than the Allen's threshold or has been less than the Allen's threshold for over 5 seconds.

The criteria for the various states are evaluated in the following order:

| | |
|---|---|
| Disconnect: | The IR light level is zero for two seconds. If the light level has been zero for less than two seconds the Not Sure state is declared. |
| No contact: | The contact electrodes of a sensor indicated that there is no contact with the patient. |
| Pulse lost: | The % IR modulation is below the Allen's threshold for over 5 seconds, or the criteria for Non-pulse are met and the previous state had been Pulse lost. |
| Non-pulse: | The sum of 125 * uncorrelation (128 sample points) and the percentage of energy about 5 Hz in the 128 sample point spectrum is greater than 100 OR the percent IR modulation is below 0.05. This criterion has been true for ten seconds continuously. If this criterion has been true for less than ten seconds, the Not Sure state is declared. |
| Pulse present: | The state is not one of the above states. |

The criteria for the various display actions are UPDATE when the state is Pulse present, HOLD when the state is Not Sure or No contact, and CLEAR when the state is Disconnect, Pulse lost, or Non-pulse.

The best saturation is displayed when 1) the signal state action is UPDATE, and 2) the best saturation is less than 40 seconds old. Saturation is held when 1) the conditions for displaying the best saturation are not met, 2) the displayed saturation is less than 40 seconds old, and 3) the signal state action is not CLEAR. Saturation is blanked when 1) the conditions for displaying the best saturation are not met, and 2) the conditions for holding the saturation are not met.

The best heart rate is displayed when 1) the best calculated heart rate has a confidence interval >50%, and 2) the signal state action is UPDATE. The heart rate is held when 1) the conditions for displaying the current heart rate are not met, 2) the displayed heart rate is less than 40 seconds old, and 3) the signal state action is not CLEAR. The heart rate is blanked when 1) the conditions for displaying the current heart rate are not met, and 2) the conditions for holding the heart rate are not met.

While the invention has been particularly shown and described with reference to specific embodiments thereof, it will be understood by those skilled in the art that the foregoing and other changes in the form and details may be made therein without departing from the spirit or scope of the invention. It will be understood that different embodiments of the present invention may employ different combinations of the above-described techniques. For example, in one embodiment, the Kalman cardiac gated averaging technique may be used to shape the oximetry data pulses for processing by either a CLS saturation calculation technique, the Kalman saturation calculation technique, or an alternate technique. Either embodiment could use an ECG pulse rate, or a pulse rate generated by the ACF as the cardiac gated averaging trigger. Other embodiments may employ the Kalman saturation calculation technique without the Kalman cardiac gated averaging technique.

Moreover, the technology disclosed in this patent is applicable to many noninvasive medical monitoring technologies. For example, in respiratory gas monitoring like capnography the measured signal is many times driven by regular breathing. In blood pressure monitoring, the sounds in auscultatory measurements, or the pressure variations in oscillometric measurements, are both driven by the beating heart as is the plethysmogram in pulse oximetry. The scope of the invention should therefore be determined not by the specification, but by the following claims.

What is claimed is:

1. In a system for measuring a physiological parameter using at least one wavelength of electromagnetic energy transmitted through living tissue, a method for determining an operational status of the system comprising:
   receiving a data signal from at least one sensor;
   determining whether the received data signal is representative of the physiological parameter by accessing whether the at least one sensor is secured to the living tissue, wherein the accessing comprises analyzing a frequency spectrum corresponding to the at least one wavelength to determine a percentage of energy contained in a subset of the frequency spectrum; and
   generating a status signal representative of the operational status of the system based on the determining.

2. The method of claim 1 wherein the accessing comprises measuring an output level corresponding to the at least one wavelength.

3. The method of claim 1 wherein the system uses at least two wavelengths electromagnetic energy to measure the physiological parameter, and the accessing comprises of monitoring a correlation between data corresponding to a first wavelength and data corresponding to a second wavelength.

4. The method of claim 1 wherein the accessing comprises of analyzing a frequency power spectrum corresponding to the at least one wavelength to determine a percentage of energy contained in a subset of the frequency power spectrum.

5. The method of claim 1 wherein the accessing comprises monitoring an amplitude of the data signal for a first interval.

* * * * *